(12) United States Patent
Starr et al.

(10) Patent No.: US 11,244,748 B2
(45) Date of Patent: Feb. 8, 2022

(54) SYSTEMS, DEVICES AND METHODS FOR ASSESSING INHALATION THERAPY

(71) Applicant: MYLAN INC., Canonsburg, PA (US)

(72) Inventors: Eric W Starr, Butler, PA (US); Molly Knewtson, Pittsburgh, PA (US)

(73) Assignee: Mylan Inc., Canonsburg, PA (US)

( * ) Notice: Subject to any disclaimer, the term of this patent is extended or adjusted under 35 U.S.C. 154(b) by 308 days.

(21) Appl. No.: 16/093,886

(22) PCT Filed: Apr. 14, 2017

(86) PCT No.: PCT/US2017/027588
§ 371 (c)(1),
(2) Date: Oct. 15, 2018

(87) PCT Pub. No.: WO2017/180980
PCT Pub. Date: Oct. 19, 2017

(65) Prior Publication Data
US 2019/0060590 A1  Feb. 28, 2019

Related U.S. Application Data

(60) Provisional application No. 62/322,394, filed on Apr. 14, 2016.

(51) Int. Cl.
*G16H 20/13* (2018.01)
*A61M 11/00* (2006.01)
(Continued)

(52) U.S. Cl.
CPC .......... *G16H 20/13* (2018.01); *A61B 5/0022* (2013.01); *A61B 5/087* (2013.01); *A61B 5/4833* (2013.01);
(Continued)

(58) Field of Classification Search
CPC .............. A61M 16/0003; A61M 11/00; A61M 15/0085; A61M 16/0051; A61M 16/0057; A61M 2205/50; A61M 2205/583; A61M 2016/0039; A61M 2205/505; A61M 2205/52; A61M 2205/581; A61M 2016/0027; A61M 16/024; A61M 16/0816; A61M 16/021; A61M 16/06; A61M 16/0833; A61M 15/0021; A61M 16/161; A61M 2205/3592; A61M 2230/42; A61M 2205/3331; A61M 2205/3553;
(Continued)

(56) References Cited

U.S. PATENT DOCUMENTS

2007/0048181 A1*  3/2007  Chang ................ G01N 27/4146
422/400
2008/0077440 A1*  3/2008  Doron ................. G07F 17/0092
705/2

(Continued)

*Primary Examiner* — Victoria Murphy

(57) ABSTRACT

Features for assessing patient compliance with therapeutic usage of an inhaler, such as a nebulizer, are disclosed. Nebulizer therapy accessories include mouthpiece, mask and adaptor (i.e. an attachment to a mouthpiece or mask) that may be coupled with the nebulizer. The nebulizer therapy accessory includes at least one sensor that detects a physical parameter generated by a user's body and generates a signal. The signal is used to determine therapy compliance, which may be communicated to the patient and/or the patient's physician.

21 Claims, 20 Drawing Sheets

(51) Int. Cl.
- *A61M 15/00* (2006.01)
- *A61M 16/06* (2006.01)
- *A61B 5/00* (2006.01)
- *A61M 16/08* (2006.01)
- *A61M 16/16* (2006.01)
- *G16H 40/67* (2018.01)
- *A61B 5/087* (2006.01)
- *G16H 20/40* (2018.01)
- *G16H 50/30* (2018.01)
- *A61M 16/00* (2006.01)
- *G16H 20/30* (2018.01)
- *A61B 5/08* (2006.01)
- *A61B 5/083* (2006.01)
- *A61M 11/06* (2006.01)

(52) U.S. Cl.
CPC ........ *A61M 11/00* (2013.01); *A61M 15/0021* (2014.02); *A61M 15/0085* (2013.01); *A61M 16/0003* (2014.02); *A61M 16/021* (2017.08); *A61M 16/06* (2013.01); *A61M 16/0816* (2013.01); *A61M 16/0833* (2014.02); *A61M 16/161* (2014.02); *G16H 20/30* (2018.01); *G16H 20/40* (2018.01); *G16H 40/67* (2018.01); *G16H 50/30* (2018.01); *A61B 5/0816* (2013.01); *A61B 5/0836* (2013.01); *A61B 5/4848* (2013.01); *A61B 2562/028* (2013.01); *A61B 2562/029* (2013.01); *A61B 2562/0247* (2013.01); *A61B 2562/0271* (2013.01); *A61M 11/005* (2013.01); *A61M 11/06* (2013.01); *A61M 2016/0027* (2013.01); *A61M 2016/0033* (2013.01); *A61M 2016/0036* (2013.01); *A61M 2205/13* (2013.01); *A61M 2205/3331* (2013.01); *A61M 2205/3334* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2205/52* (2013.01); *A61M 2205/8206* (2013.01); *A61M 2205/8243* (2013.01); *A61M 2230/42* (2013.01); *A61M 2230/432* (2013.01)

(58) Field of Classification Search
CPC ................ A61M 11/005; A61M 11/06; A61M 2205/3561; A61M 2205/8243; A61M 2016/0036; A61M 2016/0033; A61M 2205/3334; A61M 2205/13; A61M 2205/3368; A61M 2205/3584; A61M 2205/8206; A61M 2230/432; G16H 50/30; G16H 20/13; G16H 40/67; G16H 5/0022; G16H 20/40; G16H 20/30; A61B 5/4833; A61B 5/4848; A61B 5/087; A61B 5/0022; A61B 5/0816; A61B 2562/0247; A61B 5/0836; A61B 2562/0271; A61B 2562/029; A61B 2562/028; F04C 2270/041

See application file for complete search history.

(56) References Cited

U.S. PATENT DOCUMENTS

| | | | |
|---|---|---|---|
| 2008/0078382 A1* | 4/2008 | LeMahieu | A61M 16/107 128/200.24 |
| 2011/0077586 A1* | 3/2011 | Plahey | A61M 1/28 604/29 |
| 2012/0272955 A1* | 11/2012 | Cool | A61M 15/0083 128/203.12 |
| 2013/0340751 A1* | 12/2013 | D'Angelo | A61M 16/0051 128/202.22 |
| 2014/0371618 A1* | 12/2014 | Steinhauer | A61M 16/021 600/532 |
| 2015/0174348 A1* | 6/2015 | Tunnell | A61M 15/003 128/200.14 |

* cited by examiner

SYSTEMS, DEVICES AND METHODS FOR ASSESSING INHALATION THERAPY

REFERENCE TO RELATED APPLICATIONS

This application is a U.S. National Stage application under 35 U.S.C. § 371 of International Patent Application No. PCT/US2017/027588, Apr. 14, 2017, which claims the benefit of U.S. provisional patent application No. 62/322,394 filed on Apr. 14, 2016, of which is hereby incorporated by reference in its entirety.

TECHNICAL FIELD

The development relates generally to inhalers, in particular to systems, devices and methods for assessing the compliance with therapeutic use of an inhaler by a user.

BACKGROUND

Medication adherence by patients is important to successful treatment with the prescribed medications. Many patients with one of a variety of lung or pulmonary diseases (e.g., chronic obstructive pulmonary disease (COPD), cystic fibrosis, asthma, etc.) are insufficiently adherent to the prescribed medication regimen. For example, in 2011, almost one of every four COPD patients were readmitted within 30 days, costing $1.1 billion.

Such regimens often include the use of various types of inhalers, such as nebulizers. Nebulizers are drug delivery devices used to administer medication in the form of a mist inhaled through the mouth and into the lungs. Patients fail to adhere to prescribed regimens using these and other inhalers for a variety of reasons. For instance, patients often forget to use their nebulizers or may use nebulizers improperly (e.g., by not completing the full duration of treatment). Nebulizers and other inhalers currently available do not provide features to address these issues.

SUMMARY

The subject matter relates broadly to a nebulizer accessory (e.g. adaptor, mouthpiece or mask) for nebulizers and to systems and methods that use and integrate such an accessory. A nebulizer may be a drug delivery device used to administer medication in the form of a mist inhaled into the lungs. The accessory facilitates assisting a user to comply with a nebulizer therapy treatment by determining a treatment duration of the nebulizer therapy treatment. An actual treatment duration may be measured as the duration of the patient's therapy treatment, less a pause of therapy. The actual treatment duration may be compared to an expected treatment duration to determine a compliance score, which may be transmitted to a user.

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing approaches to nebulizer therapy assessment.

BRIEF DESCRIPTION OF THE DRAWINGS

The foregoing and other features of the present disclosure will become more fully apparent from the following description and appended claims, taken in conjunction with the accompanying drawings.

DETAILED DESCRIPTION

Certain embodiments involve a nebulizer therapy accessory, such as an adaptor, mouthpiece, or mask for nebulizers and to systems and methods that use and integrate such a nebulizer therapy accessory. A method for assisting a user to comply with a nebulizer therapy treatment is provided. The method may include determining a treatment duration of the nebulizer therapy treatment based on sensing the presence of one or more physical attributes or properties. As described in detail below, the detection of the physical properties may be performed on a nebulizer therapy accessory such as a nebulizer adaptor, mouthpiece, or mask. In some cases, a pause of therapy may be determined during the nebulizer therapy treatment. In such cases, an actual treatment duration may be determined by a difference between the pause duration and the treatment duration. The actual treatment duration may be compared to an expected treatment duration to compute a compliance score, which may be transmitted to a user having a user device.

In additional or alternative embodiments, a nebulizer therapy accessory, such as an adaptor, mouthpiece, or mask, for nebulizer therapy treatment is provided. In some embodiments, the nebulizer therapy accessory may include a body defining a channel and further includes a sensor to detect at least one attribute of a fluid, such as air, flowing through the channel. In additional or alternative embodiments, the nebulizer therapy accessory may include a sensor to detect proximity of the user to the nebulizer therapy accessory. In additional or alternative embodiments, the nebulizer therapy accessory may include a combination of a sensor positioned to detect at least one attribute of a fluid in combination with a sensor to detect proximity of the user to the nebulizer therapy accessory. The nebulizer therapy accessory may include a processor that executes instructions stored on a memory that causes the accessory to determine the treatment duration of nebulizer therapy treatment and a pause of therapy that may occur during the nebulizer therapy treatment.

Embodiments of the development will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the development. Furthermore, embodiments of the development may include several novel features, no single one of which is solely responsible for its desirable attributes or which is essential to practicing the invention described herein.

Figure 1:
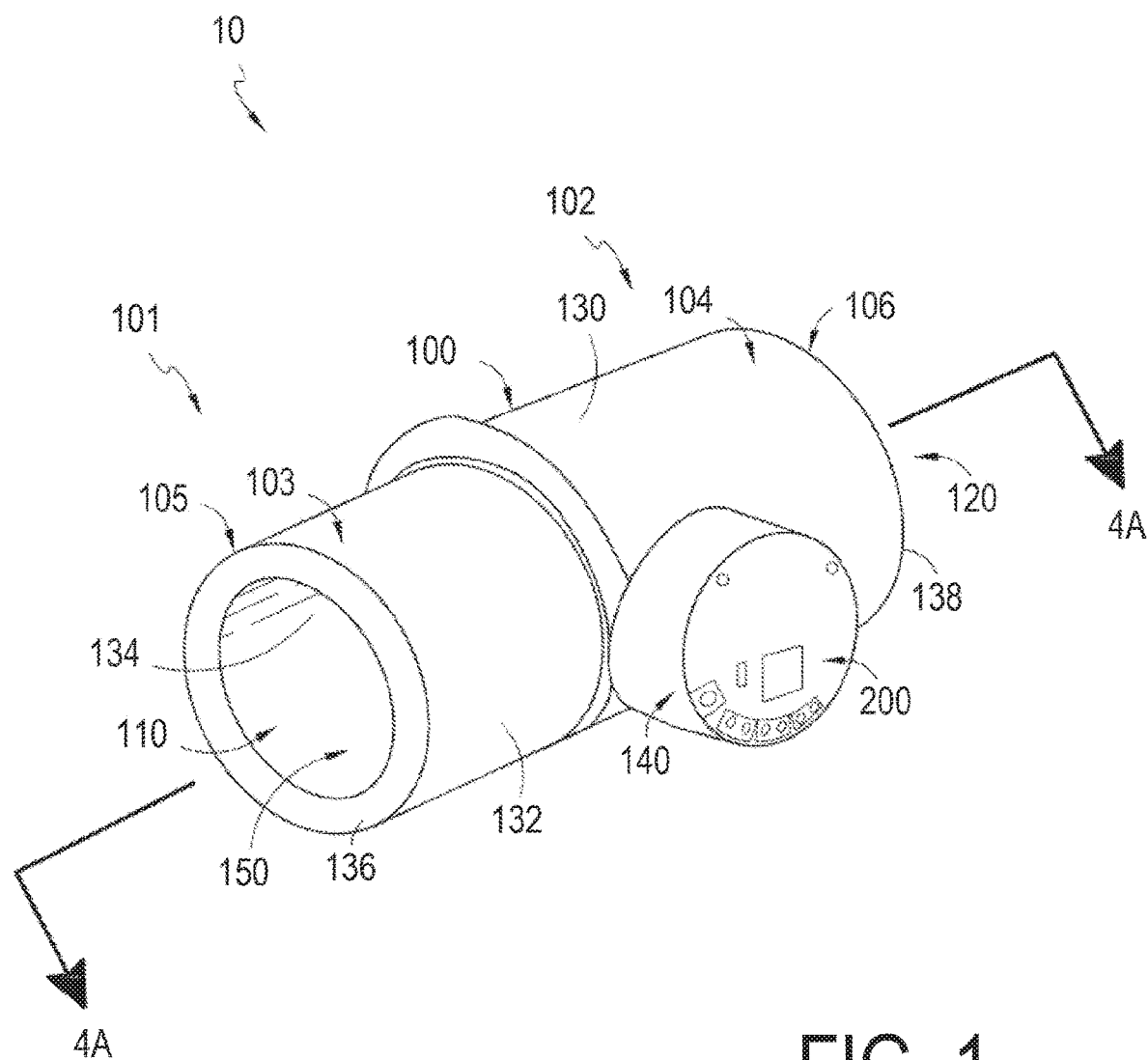
FIG. 1 is a perspective view of an embodiment of a nebulizer adaptor.

FIG. 1 is a perspective view of an embodiment of a nebulizer adaptor 10. The adaptor 10 may be used to assess patient compliance with nebulizer therapy. The adaptor 10 may integrate with a nebulizer and nebulizer accessory to measure physical attribute data pertaining to the fluid flowing between the nebulizer and nebulizer accessory and through the adaptor. The integration may be seamless, such that delivery of therapy is not substantially interrupted or otherwise impaired by inclusion of the adaptor 10 with such systems. Such physical attribute data may be analyzed to assess the patient's compliance with therapy, as described herein.

The adaptor 10 may include a body 100. The body 100 depicted in FIG. 1 generally defines a structure of the adaptor 10. The body 100 or portions thereof may be formed from a variety of materials. The body 100 may be formed from a plastic or polymer in some embodiments, the body 100 may be formed from a plastic, polymer, metal, alloy, composite, other suitable materials, or combinations thereof. The body 100 or portions thereof may be formed from a rigid material. In some embodiments, the body 100 or portions thereof may be formed from a semi-rigid material in some embodiments, the body 100 or portions thereof may be formed from a flexible material. The structure of the body 100 or portions thereof can prevent fluid from flowing transversely through the structure of the body 100, such that fluids flow in one open end of the adaptor 10 and out another open end, as described herein. Therefore, the body 100 may be formed from a generally non-porous material. The body 100 may be formed from a material that is generally impermeable to fluids. However, as further described herein, there may be openings in the body 100 to allow for one or more sensors to protrude into or otherwise detect attributes of the fluid flowing through the adaptor.

The adaptor 10 may include a proximal portion 101 and a distal portion 102. The proximal portion 101 and distal portion 102 may be different portions of the body 100. The body 100 may extend from the proximal portion 101 to the distal portion 102. The proximal portion 101 and distal portion 102 may be exclusive of each other, or they may have some overlap. The proximal portion 101 is located generally opposite of the distal portion 102. The proximal portion 101 may be located directly opposite of the distal portion 102. The proximal portion 101 and distal portion 102 each include features for coupling the adaptor 10 to a nebulizer accessory and to a nebulizer, as described herein. The proximal portion 101 may include features to couple with (e.g., connect to) a nebulizer accessory. The distal portion 102 may include features to couple with a nebulizer.

The adaptor 10 may include a first fitting 103 and a second fitting 104. The first fitting 103 may be located on the proximal portion 101. The second fitting 104 may be located on the distal portion 102. The first fitting 103 may be located generally opposite the second fitting 104. The first fitting 103 may be located across from the second fitting 104. The first fitting 103 may be located angularly 180 degrees relative to the second fitting 104. The first fitting 103 and second fitting 104 provide features for coupling the adaptor 10 to a nebulizer accessory and to a nebulizer. The first fitting 103 may couple with a nebulizer accessory. The second fitting 104 may couple with a nebulizer. The first and second fittings 103, 104 may have various ends and openings as described herein to facilitate coupling with their respective components. The first fitting 103 and second fitting 104 may be rounded, for example circular. In some embodiments, the first fitting 103 and second tilting 104 may have other suitable shapes for coupling with their respective components. One or more of the fittings 103, 104 may have relatively smooth surfaces to snap lit in or around a component, such as a nebulizer or nebulizer accessory. In some embodiments, one or more of the fittings 103, 104 may have other features to couple to respective components in a variety of ways, such as threads ((e.g., for screw fit), conical sections (e.g., for friction fit), latches or straps (e.g., for securement), moveable pins (e.g., for engagement), etc. The first and second fittings 103, 104 may include a variety of features of the body 100, as described herein, which may be integral with the body 100. In some embodiments, these features of the fittings 103, 104 may be separate components that are attached to or with the adaptor 10.

The adaptor 10 may include a first end 105 and a second end 106. The first end 105 is located generally opposite the second end 106. The first end 105 and the second end 106 may be opposite ends of the body 100. As shown, the first end 105 may be located directly opposite the second end 103. In some embodiments, the first end 105 may not be located directly opposite the second end 106. The first end 105 may be an end portion of the proximal portion 101. The first end 105 may be an end portion of the first fitting 103. The second end 106 may be an end portion of the distal portion 102. The second end 106 may be an end portion of the second fitting 104. The first end 105 and second end 106 may be integral with, respectively, the first fitting 103 and second fitting 104. In some embodiments, the first end 105 and second end 106 may be separate components that are coupled with, respectively, the first fitting 103 and second fitting 104. The first end 105 and second end 106 may be rounded, for example circular. In some embodiments, the first end 105 and second end 106 may have other suitable shapes for coupling with their respective components. The first and second ends 105, 106 may define one or more openings as described herein.

The adaptor 10 may include a first welling 110 and a second opening 120. The first opening 110 and second opening 120 may be openings defined by one or more portions of the body 100. The first opening 110 and second opening 120 may be defined by end portions of the body 100. The first opening 110 and second opening 120 may be defined, respectively, by the first and second ends 105, 106. The first and second openings 110, 120 may be defined, respectively, by the first and second fittings 103, 104. The proximal portion 101 may include the first opening 110. The distal portion 102 may include the second opening 120. The first opening 110 and second opening 120 may be rounded, for example circular. In some embodiments, the first opening 110 and second opening 120 may have other suitable shapes for coupling with their respective components, for allowing fluid to flow through the openings, etc.

The adaptor 10 may Include a sidewall 130. The sidewall 130 may be a portion of the body 100. The sidewall 130 may generally define an outer boundary of the body 100. The sidewall may generally define a passage for fluid flow through the body 100, as described herein. The sidewall 130 or portions thereof may form all or portions of, or include all or portions of, one or more of the features described herein, for example, the proximal portion 101, the distal portion 102, the first fitting 103, the second fitting 104, the first end 105, the second end 106, the first opening 110, the second opening 120, other features, or combinations thereof. The sidewall 130 may be a generally rounded, hollow structure and extending generally along a flow path direction, as described herein.

The adaptor 10 may include an outer portion 132 and an inner portion 134. The inner and outer portions 134, 132 may be one or more portions of the body 100, such as the sidewall 130. The inner and outer portions 134, 132 may thus be portions (e.g., example surfaces, regions, areas, etc.) of the sidewall 130. The inner and outer portions 134, 132 may be defined by one or more of the body 100, the sidewall 130, and other components of the body 100 and adaptor 10. The inner and outer portions 134, 132 may be inner and outer surfaces, respectively, of the body 100 and/or sidewall 130. The inner portion 134 may be a portion or portions of the body 100 that are generally on the interior of the body 100. The outer portion 132 may be a portion or portions of the body 100 that are generally on the exterior of the body 100. The inner and outer portions 134, 132 may extend from the proximal portion 101, or portions thereof, to the distal portion 102, or portions thereof. The inner portion 134 may define at least in part a fluid passage through the adaptor 10, such as a channel, as described herein. The inner and outer portions 134, 132 may be coupled by one or more edges, as described herein.

The adaptor 10 may include a first edge 136 and a second edge 138. The first and second edges 136, 138 may be located, respectively, at the proximal and distal portions 101, 102. The first and second edges 136, 138 may be located at the first and second ends 105, 106. The first and second edges 136, 138 may couple the inner and outer portions 134, 132 at their respective ends of the adaptor 10. The first and second edges 136, 138 may be "hard" edges with surfaces that are generally perpendicular to a longitudinal axis of the adaptor 10. In some embodiments, the first and second edges 136, 138 may be "soft" edges, for example with rounded features. In some embodiments, the first and second edges 136, 138 may be combinations of sharp and rounded shapes. The first and second edges 136, 138 may form all or portions of, respectively, the first and second ends 105, 106. Thus, the first and second edges 136, 136 may be integral with the body 100. In some embodiments, the first and second edges 136, 138 may be separate parts that are connected to the body 100.

The first end second fittings 103, 104 may include one or all of the various features described herein in a variety of configurations to couple with respective components in a variety of ways. For example, the first and second fittings 103, 104 may include one or all of the various features of the proximal portion 101, the distal portion 102, the first fitting 103, the second fitting 104, the first end 105, the second end 106, the first opening 110, the second opening 120, the first edge 136, the second edge 138, other features, or combinations thereof. These and other features that form some or all of the first and second fittings 103, 104 may be configured such that the first and second fittings 103, 104 couple with other components, such as a nebulizer and nebulizer accessory, in a variety of ways. The first and second fittings 103, 104 may be configured to snap fit to a nebulizer and nebulizer accessory.

In some embodiments, the first and second fittings 103, 104 can suitably couple with their respective components. Examples of suitable couplings include screws, friction fits, clamping, straps, adhesives, fasteners, or some combination thereof. Further, each fitting 103, 104 need not couple to their respective component in the same way. For example, the first fitting 103 may couple with a first component (e.g., a nebulizer) via snap fit, and the second fitting 104 may couple with a second component (e.g., a nebulizer accessory) via a strap. This is just an example, and a variety of configurations and approaches may be implemented. One or more of the fittings 103, 104 can fit at Fast partially inside a component, such as a nebulizer or nebulizer accessory. One or more of the fittings 103, 104 can fit at least partially around a component, such as a nebulizer or nebulizer accessory.

The adaptor may include one or more sensor fittings 140. The sensor fitting 140 can couple with one or more electronics systems, such as the electronics system 200 described herein. As shown, there may be one sensor fitting 140. The sensor fitting 140 may be located on the body 100. The sensor fitting 140 may be located on the side all 130. The sensor fitting 140 may be located generally in between opposite ends 105, 106 of the adaptor 10. The sensor fitting 140 may be located partially or completely on the proximal portion 101. The sensor fitting 140 may be located partially or completely on the distal portion 102. The sensor fitting 140 may be located on both the proximal and distal portions 101, 102.

The sensor fitting 140 may define a recess or other cavity in which the sensor 210 is located. The sensor tilting 140 may be sized and shaped to receive therein a complementary-shaped electronics system 200. The sensor failing 140 may be generally round and define a recess. The body 100 may include openings, which can be located in or near the sensor fitting 140, through which one or more sensors of the electronics system 200, as described herein, may protrude or otherwise communicate with to detect various attributes of flow through the adaptor 10. There may be such openings in portions of the sensor fitting 140, in the sidewall 130, and/or in other portions of the body 100.

The adaptor 10 may include the electronics system 200. The electronics system 200 may include various electronics, components, modules, etc., to perform a variety of functions. Examples of these functions include one or more of detecting, measuring, collecting, analyzing and communicating various data, information, analyses, measurements, etc. related to the flow of fluid through the adaptor 10. Further details of the electronics system 200 are described herein, for example, with respect to FIG. 3. The electronics system 200 may be coupled with the sensor fitting 140. For example, the system 200 may be received into the fitting 140. The system 200 may be removably coupled with the fitting 140. In some embodiments, portions of the system 200 may be coupled with the fitting 140 and other portions may be coupled with other features of the body 100, for example with a separate battery compartment, as described herein.

The adaptor 10 may include a channel 150. The channel 150 is a fluid passageway through the adaptor 10. The channel 150 thus provides fluid communication between the first and second openings 110, 120 of the adaptor 10. Fluids, such as gases, liquids, or mixtures thereof, may flow from the first opening 110 to the second opening 120 via the channel 150. The channel 150 may thus provide a passageway extending through the adaptor 10. Medicament, such as mists, may flow from a first component, such as a nebulizer, through the channel 150, and then to a second component, such as the nebulizer accessory.

The channel 150 may be defined by one or more parts of the adaptor 10. The channel 150 may be defined at east in part by the inner portion 134. Additionally or alternatively, the channel 150 may be defined at least in part by all or portions of the proximal portion 101, the distal portion 102, the first fitting 103, the second fitting 104, the first end 105, the second end 106, the first opening 110, the second opening 120, the sidewall 130 other features of the adaptor 10, or combinations thereof. In some embodiments, the channel 150 extends from the first opening 110 of the proximal portion 101, through the inner portion 134 and to the second opening 120 of the distal portion 102.

The channel 150 may have a variety of shapes and configurations. The channel 150 may have a variety of cross-sectional shapes and sizes, where "cross-sectional" here refers to a cross-section view of the channel 150 that is perpendicular to the direction of fluid flow through the channel 150. The cross-sectional shapes may be round cross-sections (e.g., circular). Additionally or alternatively, the channel 150 may have square cross-sections, segmented cross-sections (e.g., polygonal), other suitable shapes, or combinations thereof. Thus, the cross-sectional shape and size need not be the same along the entire length of the channel 150. For example, a first cross-section of the channel 150 in a first location in the fluid flow may be circular with a diameter of "D," and a second cross-section of the channel 150 located relatively upstream or downstream of the fluid flow may be circular (or other shapes) with a diameter greater (or less than) "D".

The channel 150 may extend along a variety of directions. The channel 150 may extend along a generally linear (e.g., straight) direction. In some embodiments, the channel 150 may not extend along a generally linear (e.g., straight) direction. In some embodiments, the channel 150 may extend along a segmented path. An example of a segmented path is a path with one or more sharp turns in the channel 150. In some embodiments, the channel 150 may extend along a smoothly curved path. An example of a smoothly curved path is a path with one or more smooth turns in the channel 150. In some embodiments, the channel 150 may extend along other paths, or along combinations of these and/or other directions.

In the example depicted in FIG. 1, the channel 150 defines a single passage extending through the adaptor 10. However, other implementations are possible. For example, the channel 150 may include more than one passage or opening extending through the adaptor 10. In some embodiments, the channel 150 may be segmented or separated into multiple sub-channels. For example, an inner wall (not shown) may extend along and within the channel 150 such that there are effectively two passages extending through the adaptor 10 and fluidly connecting the two ends of the adaptor 10. In some embodiments, the channel 150 may be divided into separate sub-channels, for example, for redundant analysis of the fluid flowing through the channel 150. For instance, the channel 150 may have an inner wall that divides the channel 150 into two sub-channels, where fluid flows separately through each sub-channel. In such embodiments, there may be separate electronics systems 200, for instance separate sensors, within each sub-channel for redundant, for example more reliable, analysis of the fluid flowing through the channel 150.

The channel 150 may be defined in part by other components with which the adaptor 10 is coupled. For example, the adaptor 10 may partially receive a nebulizer in one end and a nebulizer accessory into an opposite end, as described herein. Thus, the channel 150 may be defined in part by those portions of the nebulizer and nebulizer accessory that extend into the adaptor 10 such as into the first and second fittings 103, 104. In other words, the medicament may not contact some portions of the channel 150 when using the adaptor 10. Portions of the channel 150 defined by the adaptor 10 may be covered by the corresponding portions of other components with which the adaptor 10 is coupled. The configuration, direction, size, shape, etc. of the channel 150 is described in further detail herein, for example with respect to FIGS. 4-12.

Figure 2:
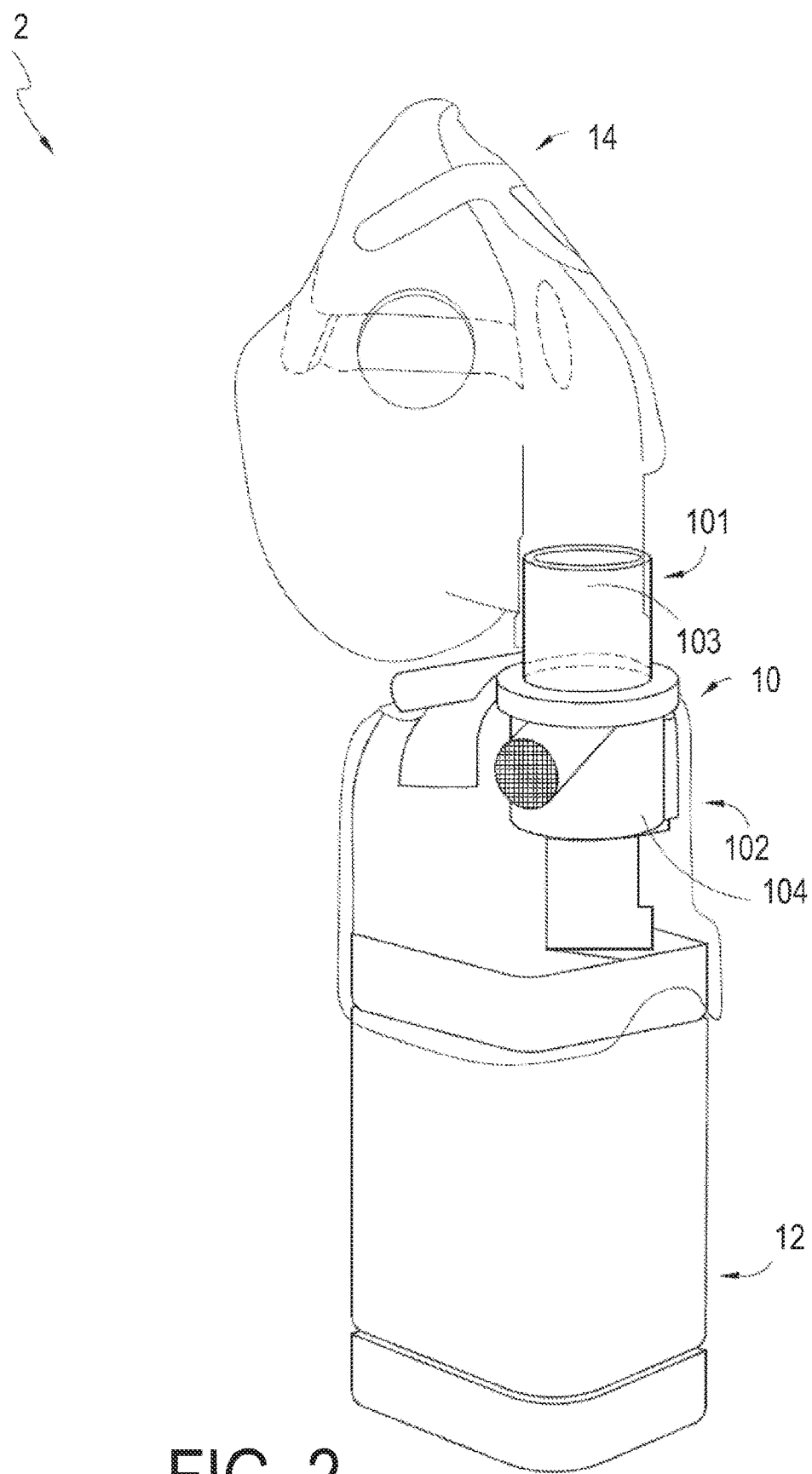
FIG. 2 is a perspective view of the nebulizer adaptor of FIG. 1 coupled with an example of a nebulizer and with an example of a facemask.

FIG. 2 is a perspective view of a nebulizer assessment system 2. The system 2 includes the adaptor 10 coupled with an embodiment of a nebulizer 12 and coupled with an embodiment of a nebulizer accessory 14.

In the present embodiment, the nebulizer accessory 14 is a mask. However, the disclosure of the mask should not be considered limiting on the current disclosure as in various other embodiments, the nebulizer 14 may be various other nebulizer accessories. For example, FIGS. 4-8 illustrate an embodiment where the nebulizer accessory 14 is a mouthpiece.

The adaptor 10 may couple directly with the nebulizer 12 and directly with the nebulizer accessory 14. In some embodiments, the adaptor 10 may couple indirectly with the nebulizer 12 and/or indirectly with the nebulizer accessory 14. In some embodiments, the adaptor 10 may couple with the nebulizer 12, the nebulizer accessory 14, and/or with other components. For example, the adaptor 10 may couple with intermediate fittings located in between the nebulizer 12 and the adaptor 10 and/or in between the nebulizer accessory 14 and the adaptor 10. Further, the adaptor 10 may couple with only portions of the various components.

The nebulizer 12 may be any of a variety of nebulizers or other inhalers. The nebulizer 12 may be of variety of types, including but not limited to vibrating mesh, static mesh, piezo/ultrasonic, jet/compression. The nebulizer 12 may be any of a number of commercially available nebulizers, including but not limited to the Handheld Nebulizer, the MICRONEB® from Clement Clarke, the EFLOW® Rapid or LC SPRINT® from Pari, the MICROELITE® by Philips, the IH50® or IH30® by Bauer, the AERONEB® Go by Aerogen, the MICROAIR® or NE-U17® or ULTRA AIR® by Omron, the MICROSONIC® by Prizma, the VIXONE by DeVilbiss, the STRATOS® by Invacare, the AEROMIST PLUS® by Medline. These and other nebulizers 12 may deliver any of a variety of solution medications, including but not limited to Albuterol®, Alupent®, Brokosol®, Isuprel®, Pulmicort Respules®, Proventil®, Ventolin®, Xopenex®, DuoNeb® and Intal®.

The nebulizer accessory 14 may be any of a variety of nebulizer accessories or other components related to use of a nebulizer or other inhaler.

Various features of the adaptor 10 may couple with these and other components. Features of the proximal portion 101, such as the first fitting 103, may couple with the nebulizer accessory 14. Features of the distal portion 102, such as the second fitting 104, may couple with the nebulizer 12. Additionally or alternatively, other features of the adaptor 10 may couple with the various components. For example, the body 100, the proximal portion 101, the distal portion 102, the first fitting 103, the second fitting 104, the first end 105, the second end 106, the first opening 110, the second opening 120, the sidewall 130, the outer portion 132, the inner portion 134, the first edge 136, the second edge 138, the sensor fitting 140, the channel 150, other features, or combinations thereof, may couple with the various components. These and other features of the adaptor 10 may couple with the venous components in a variety of ways, as described herein. In some embodiments, the various components snap into or onto the respective feature of the adaptor 10. For example, the one or more portions of the adaptor 10 may fit over, into, or combinations thereof, the one or more portions of the nebulizer 12 and/or the nebulizer accessory 14. In some embodiments, the one or more portions of the adaptor 10 can couple with standard-sized fittings on the nebulizer 12 and/or nebulizer accessory 14. For example, portions of the adaptor 10, such as the second fitting 104, may be sized and shaped to attach to a standard 22 millimeter (mm) nebulizer fitting. In some embodiments, portions of the adaptor 10, such as the first fitting 103 and/or second fittings 104, may be sized and/or shaped to attach to other International Organization for Standards (ISO) standard sizes for respiratory fittings, as described herein.

Figure 3:
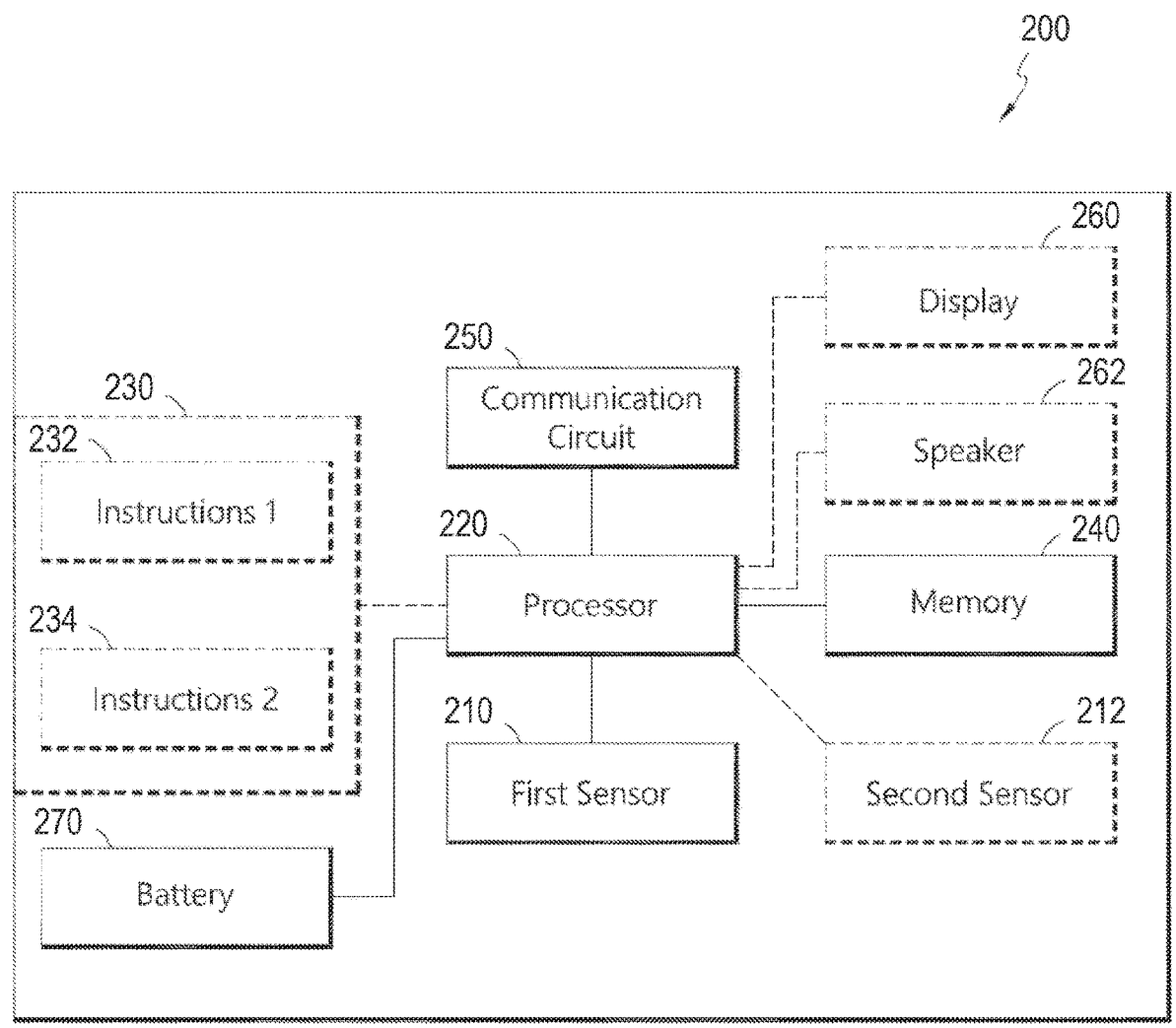
FIG. 3 is a block diagram showing an embodiment of an electronic sensing system of the nebulizer adaptor of FIG. 1 that includes one or more physical property sensors, a processor and a communication circuit.

FIG. 3 is a block diagram showing an embodiment of the electronics system 200 that may be included with the various adaptors and accessories described herein, such as the adaptor 10. The system 200 may have components to assess, evaluate, etc. therapeutic usage of the accessory with a nebulizer, such as the nebulizer 12, or other inhaler. The system 200 may provide other functions, such as (but not limited to) collecting and analyzing data related to the flow of fluid through the accessory, collecting and analyzing data related to user touch and/or proximity of the user to the nebulizer therapy accessory, and/or communicating information related to such flow data to another communications device, as further described herein.

The system 200 may include a first sensor 210. In some embodiments, the system 200 may also include a second sensor 212, a third sensor (not shown), etc. For illustrative purposes, the system 200 is depicted as including two sensors. The sensor 212 may have the same features and/or functionalities as the sensor 210. In some embodiments, there may be more than two sensors, for example three, four, five, or more sensors, each of which may have the same features and/or functionalities as the other sensors. In some embodiments, the system 200 may include multiple sensors, some of which may have different features and/or functionalities as one or more of the others. The one or more sensors generally detect one or more attributes, such as pressure, carbon dioxide, humidity, and/or temperature, among others, of fluid flowing through the accessory, as described herein. The one or more sensors may also detect user touch or proximity of the user to the nebulizer accessory, as described herein. The one or more sensors may thus be located in the system 200 such that the sensors can detect such attributes of the flowing fluid, as described herein.

The sensors 210, 212 may be any of a variety of sensors for sensing the various attributes of the fluid flowing through the accessory 10 and/or user touch or proximity of the user. One or more of the sensors 210, 212 may be a pressure sensor, temperature sensor, humidity sensor, mass airflow sensor, carbon dioxide sensor, or proximity sensor, or combinations thereof. In additional or alternative embodiments, one or more of the sensors 210, 212 may be a mechanical pressure sensor, electrical pressure sensor, electro-mechanical pressure sensor, micro-electro-mechanical pressure sensor (MEMS), transducer, switch, diaphragm, transmitter, indicator, piezometer, manometer, piston, bourdon tube, bellow, force collection sensor, piezoresistive strain gage, variable capacitor sensor, electromagnetic sensor (e.g., using inductance, LVDT, Hall Effect, or by eddy current principle), piezoelectric, optical, potentiometric, resonant, other suitable types of pressure sensors, or combinations thereof.

For example, at least one of one or more of the sensors 210, 212 may be a temperature sensor, such as a thermistor or thermocouple. Additionally or alternatively. In some embodiments, one or more of the sensors 210, 212 may be a mechanical temperature sensor, an electrical temperature sensor, a thermometer, a bimetal, a resistance thermometer, integrated circuit sensor, humidity sensor, carbon dioxide sensor, proximity sensor, other suitable types of temperature sensors, or combinations thereof.

The system 200 may include a processor 220 in data communication with one or more of the sensors 210, 212. The term "data communication" as used herein may refer to wireless or wired communication, or combinations thereof. The processor 220 may be a general purpose processing unit or a processor specially designed for flow sensing and/or analysis applications or a processor specially designed for wireless communications (such as a Programmable System On Chip (PSOC) from Cypress Semiconductor or other suitable processors), in addition, an optional program module 230, a memory 240, a communication circuit/unit 250, an optional display 260, en optional speaker 262, and/or a battery 270 (or other suitable power storage unit) may also be included in the system 200 and in data communication with the processor 220. Some or all of the components of the system 200 may be included together in a single package or sensor suite, such as within the same enclosure. In some embodiments, some of the components may be included together in an enclosure and the other components may be separate, such as part of the adaptor 10 for example the body 140. For instance, the battery 270 may be a part of the adaptor 10, such as in a battery compartment of the body 140, and in electrical communication with the other components of the system 200. Thus, the system 200 may be a distributed system. This is merely one example and other configurations may be implemented. In related aspects, the battery 270 may be configured for wireless power charging, and may comprise one or more coils (not shown) for receiving wireless power from a wireless power transmitting device.

The system 200 may include the program module 230 having venous instruction submodules. As shown, the program module 230 may include a first instructions submodule 232 and a second instructions submodule 234. Fewer or more instructions submodules may be included. The submodules 232, 234 may be in data communication with the processor 220. The submodules 232, 234 may provide instructions for the processor to perform various functions related to the evaluation of the use of the adaptor 10 with a nebulizer, as described herein.

The system 200 may include the memory 240, which may include a long-term storage memory and a short-term working memory. The memory 240 may be used by the processor 220 to store a working set of processor instructions. In some embodiments, the instruction submodules 232, 234 stored in the program module 230 may additionally or alternatively be stored in the memory 240. In some embodiments, the module 230 may be embedded or included as part of the processor 220 and/or the memory 240. The processor 220 may write data to the memory 240.

The system 200 may include the communication circuit 250, which may be a wireless or wired system that allows for communication with other devices, such as a receiving device as described herein. The circuit 250 may include at least one of a transmitter, a receiver, or a transceiver. In some embodiments, the device 250 connects wirelessly to another device. In some embodiments, the circuit 250 provides for radio, LAN, network and/or other connections. The circuit 250 may also be a port, lack or other plug for inserting a cable to connect to another device. The communications circuit 250 may be instructed by the processor 220 to connect and communicate with the receiving device. Such instructions may be provided to the processor 220 from, for example, the program module 230 and/or the memory 240.

As noted above, the system 200 may include the optional display 260 and/or speaker 262. The display 260 may be a visual output of the system 200. In some embodiments, the display 260 may be a screen, a touch screen, a flashing display, other visual outputs, or combinations thereof. There may be more than one display 260. The speaker 262 may be an audio output of the system 200. There may be more than one speaker 262. The display 260 and speaker 262 may work together, for example coordinating visual and audio output from each, respectively. The display 260 and/or speaker 262 may provide outputs related to the evaluation of usage of the nebulizer with the accessory, as described herein.

The system 200 may include a battery 270. The battery 270 provides power to the system 200. The battery 270 may be any number of suitable types of batteries, including but not limited to primary batteries, secondary batteries, other suitable types, and with any of a variety of types of cells. The remaining charge on the battery 270 may be indicated by the system 200 such as via the display 260 and/or the speaker 262, or it may be communicated to another device, as described herein.

As mentioned, the processor 220 may be configured by various components of the system 200 to perform various functions related to evaluation, assessment, etc. of the use of a nebulizer with the adaptor 10. The processor 220 may be configured by one or more of the instructions submodules DC program module 230, by instructions stored in the memory 240, and/or by instructions received via the communications circuit 250. For example, one or more of the instructions submodules 232, 234 may include instructions that configure the processor 220 to detect at least one attribute of a fluid flowing through the adaptor 10 using one or more of the sensors 210, 212. Examples of the attribute include pressure, temperature, etc. Detecting the attribute may involve, for instance, providing power to the sensors 210, 212 to detect the various attributes, receiving electrical and/or mechanical signals from the sensors 210, 212 indicative of the detected attributes, or other suitable tasks related to detecting the attributes. In some embodiments, the instructions may configure the processor 220 to determine a volumetric flow rate of the flowing fluid based at least in part on one or more detected pressures. In some embodiments, the instructions may configure the processor 220 to determine a direction of flow of the fluid through the channel based at feast in part on one or more detected temperatures.

As further example, one or more of the instructions submodules 232, 234 may include instructions that configure the processor 220 to determine flow data based at least in part on the detected attribute of the fluid and/or proximity of the user to the nebulizer therapy accessory. As mentioned, the various instructions submodules, such as the submodules 232 and 234, may be stored or embedded with the processor 220 and/or the memory 240. In some embodiments, the instructions may configure the processor 220 to determine a volumetric flow rate of the flowing fluid. The instructions may further configure the processor 220 to determine a first pressure of the flowing fluid at a first location in the accessory and a second pressure of the flowing fluid at a second location in the accessory. The processor 220 may also be configured to determine a flow resistance of a portion of the channel located generally in between the first and second locations. The processor 220 may be configured to compare the pressures to each other, to pressure thresholds, or both.

In some embodiments, the instructions configure the processor 220 to compare generated voltages based on pressure detection to each other and/or to thresholds. The processor 220 may also be configured to perform other suitable tasks related to determining pressure-related flow data.

In some embodiments, the instructions may configure the processor 220 to determine a first temperature of the fluid at a first point in time, to determine a second temperature of the flowing fluid at a second point in time, to compare the temperatures to each other and/or to thresholds, to compare generated voltages based on temperature detection to each other and/or to thresholds, and/or other suitable tasks related to determining temperature-related flow data. In some embodiments, the instructions may configure the processor 220 to determine an indicator of compliance, such as a "compliance score," of the therapeutic usage of the nebulizer based on the pressure, humidity, proximity, carbon dioxide, and/or temperature-related data.

As a further example, one or more of the instructions submodules 232, 234 may include instructions that configure the processor 220 to instruct the communication circuit 250 to send information regarding the flow data and/or indicator of compliance to a receiving device. In some embodiments, the instructions may configure the processor 220 to code the information regarding the flow data and transmit the information to a receiving device. The receiving device may analyze the information regarding flow data to generate an indicator of a compliance with therapy, as described herein. In some embodiments, one or more of the instructions submodules 232, 234 may include instructions that configure the processor 220 to calculate the indicator, as described herein. In some embodiments, the instructions may configure the processor 220 to generate an indicator of compliance with therapy associated with the flowing fluid based al least in part on the volumetric flow rate and/or on the determined direction of flow of the fluid through the accessory.

For illustrative purposes, FIG. 3 depicts a device comprising separate components to include sensors 210 and 212, program module 230, processor 220, memory 240, communications circuit 260, and other components. However, other implementations are possible. In some embodiments, these separate components may be combined in a variety of ways to achieve particular design objectives. For example, in an alternative embodiment, the program module 230 and/or memory 240 components may be combined with components of the processor 220 to save cost and improve performance. The various instructions modules and submodules may be embedded or stored in a variety of locations, such as with the processor 220 and/or the memory 240. These are merely examples and a variety of configurations may be implemented.

Figure 4:
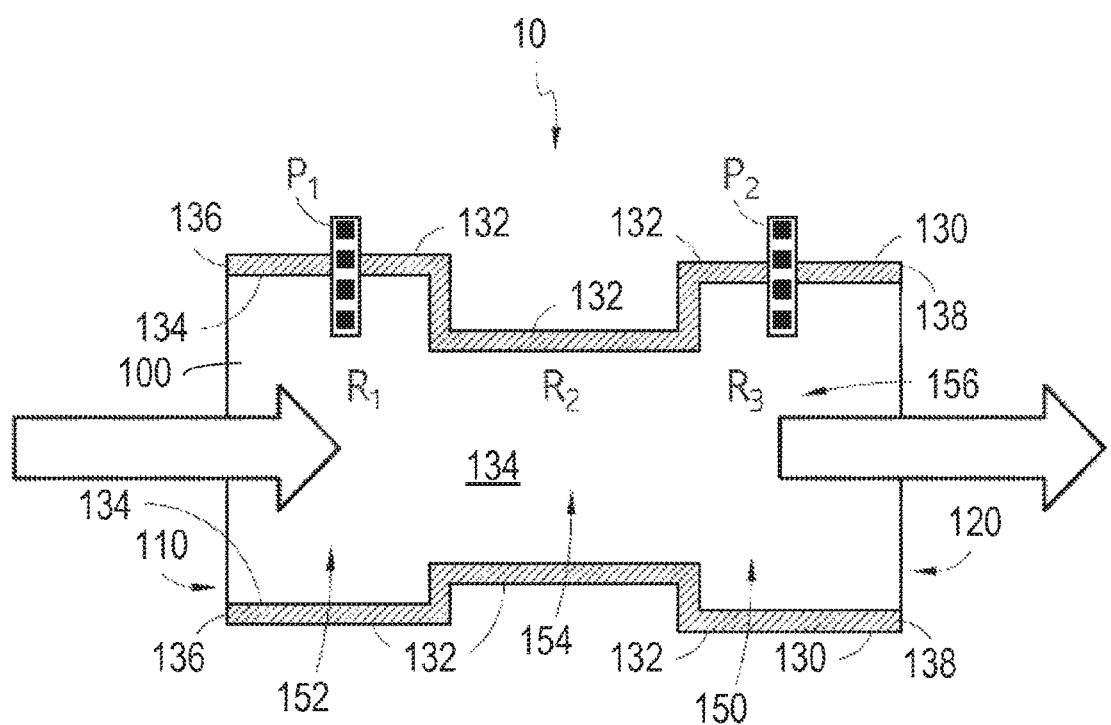
FIG. 4 is a sectional view of an embodiment of a nebulizer adaptor.

FIG. 4 is a cross-section view of an embodiment of the body 100 of the nebulizer adaptor 10. The cross-section is taken as shown in FIG. 1 along the time 4A-4A. As shown in FIG. 4, a portion of the adaptor 10 is shown, including portions of the body 100, first opening 110, the second opening 120, the sidewall 130, the outer portion 132, the inner portion 134, the first edge 136, the second edge 138 and the channel 150. The adaptor 10 may have regions of varying cross-sectional geometry, e.g., sizes, shapes, dimensions, etc. As shown, the first and second openings 110, 120 may have the same or similar sized widths. In some embodiments, first and second openings 110, 120 may have different sized widths. The sidewall 130, for example the outer portion 132, the inner portion 134, the first edge 136, and/or the second edge 138, may extend generally along the shown contour along the sides of the adaptor 10 from the first opening 110 to the second opening 112.

Fluid may flow through the channel 150. The fluid may flow through the channel 150 in the direction indicated by the arrows in FIG. 4, which may indicate an inspiration by a patient using a nebulizer with the adaptor 10. Expirations may be in the opposite direction as that indicated by the arrows. The adaptor 10 may be coupled with a nebulizer and a nebulizer accessory such that fluid, e.g., a medication mist, may flow from the nebulizer end through the channel 150 in the direction of the arrows as indicated. The fluid may flow through one or more regions or the channel 150, as described herein.

The channel 150 may have one or more regions. The channel may include a first channel region 152. The region 152 may be a region of the channel 150 that initially receives fluid flowing through the channel 150, for example during inspiration. The region 152 may be a region of the channel 150 from which fluid flowing through the channel 150 exits the adaptor 10, for example during expiration. The region 152 may have a geometry, e.g., a width, along the direction of fluid flow that is similar to that of the first opening 110. In some embodiments, the region 152 may have a geometry that is different from that of the first opening 110. The geometry of the region 152 may be generally uniform. In some embodiments, the geometry of the region 152 may vary. The geometry of the region 152 may be sized and shaped to connect the adaptor 10 to a standard sized respiratory fitting. For instance, the width of the first opening 110 and/or portions of the region 152 may allow for the adaptor 10 to attach to a standard 22 mm respiratory fitting. Such configurations may allow for the adaptor 10 to attach to a respiratory fitting that conforms with an ISO standard, such as ISO standard #13544-2:2002. The adaptor 10 may receive a portion of a nebulizer, such as the nebulizer 12, inside the first opening 110 and into a portion of the first channel region 152.

The channel may include a second channel region 154. The second channel region 154 may be located downstream of the first channel region 152, for example during inspiration. Thus, the second channel region 154 may be a region of the channel 150 that receives fluid flowing through the channel 150 after the fluid has flowed through the first channel region 152. The second channel region 154 may be located upstream of the first channel region 152, for example during expiration. Thus, the second channel region 154 may be a region of the channel 150 that receives fluid flowing through the channel 150 after the fluid has flowed through a third channel region 156, as described herein. As shown, the second channel region 154 may be adjacent the first channel region 152. The second channel region 154 may have a geometry, e.g., a width, that is smaller than the geometry, e.g., a width, of the first channel region 152. The geometry of the region 154 along the direction of fluid flow may be generally uniform. In some embodiments, the geometry of the region 154 may vary.

The channel may include a third channel region 156. The third channel region 156 may be located downstream of the first and second channel regions 152 and 154, for example during inspiration. The third channel region 156 may be located upstream of the first and second channel regions 152 and 154, for example during expiration. Thus, the second channel region 154 may be in between the first and third channel regions 152, 156. The third channel region 156 may be a region of the channel 150 that receives fluid flowing through the channel 150 after the fluid has flowed through the second channel region 154. The third channel region 156 may be a region of the channel 150 that receives fluid, e.g., expired air, flowing into the adaptor 10 from a nebulizer accessory. As shown, the third channel region 156 may be adjacent the second channel region 154. The third channel region 156 may have a geometry, e.g., a width that is greater than the geometry, e.g., width, of the second channel region 154. The region 156 may have a geometry that is similar to that of the second opening 120. In some embodiments, the region 156 may have a geometry that is different from that of the second opening 120. The geometry of the region 156 along the direction of fluid flow may be generally uniform. In some embodiments, the geometry of the region 156 may vary. The geometry of the region 152 may be sized and shaped to connect the adaptor 10 to a standard sized respiratory fitting. For instance, the width(s) of the second opening 120 and/or portions of the region 156 may allow for the adaptor 10 to attach to a standard 22 mm respiratory fitting. Such configurations may allow for the adaptor 10 to attach to a respiratory fitting that conforms with an ISO standard, such as ISO standard #13544-2:2002. The adaptor 10 may receive a portion of a nebulizer accessory, such as the nebulizer accessory 14, inside the second opening 120 and into a portion of the third channel region 156.

The regions 152, 154, 156 may be mutually exclusive of each other. In some embodiments, the regions 152, 154, 156 may overlap with each other. For instance, the first and second regions 152, 154 may overlap, and/or the second and third regions 154, 156 may overlap. There may be various types of transitions between the regions. As shown, the geometry of the channel 150 may change abruptly between the first and second regions 152, 154 and between the second and third regions 154, 156. In some embodiments, the transitions may be smooth. For instance, the transitions between the first and second regions 152, 154 and between the second and third regions 154, 156 may be angled, rounded, etc., or combinations thereof, to provide for smoother flow. These and other transitions may be in between and separating the various regions.

The channel 150 may provide various levels of resistance to fluid flowing through the channel 150. The resistance(s) may be due to particular geometry or geometries, e.g., widths, cross-sectional areas, shapes, etc., of the various regions 152, 154, 156 and/or other portions of the channel 150 or features thereof. The first channel region 152 may provide a resistance having a value of R1. The second channel region 154 may provide a resistance having a value of R2. The third channel region 156 may provide a resistance having a value of R3, R2 may be greater than each of R1 and R3. In some embodiments, R2 may be 125% of R1 and/or of R3. In other embodiments, R2 may be other percentages of R1 and/or of R3, for instance 110%-200%, or any other greater or lower percentage. R1 may be equal to R3. In some embodiments, R1 may not be equal to R3.

The adaptor 10 may have one or more sensors, such as the sensors 210 and/or 212. As shown in FIG. 4, the adaptor 10 may have a first pressure sensor P1 and a second pressure sensor P2. The first and/or second pressure sensors P1, P2 may have the same or similar features and/or functionalities as the sensors 210 and/or 212. The pressure sensors P1, P2 may be part of the system 200. The pressure sensors P1, P2 and other components of the system 200 may be coupled with the body 100 of the adaptor 10. The pressure sensors P1, P2 may detect the pressure of the fluid flowing through the channel 150. As shown, the first pressure sensor P1 may be located in the adaptor 10 to detect the pressure in the first channel region 162. The second pressure sensor P2 may be located in the adaptor 10 to detect the pressure in the third channel region 156.

In some embodiments, additional pressure sensors may be located in these or other regions of the channel 150. Thus, the configuration shown in FIG. 4 is merely an example, and other configurations may be implemented. The pressure sensors P1, P2 may protrude into the channel 150 through openings in the body 100 (not shown). In some embodiments, there may be openings in the body 100 and the pressure sensors P1, P2 may be adjacent the openings but not protrude into the channel 150. These are merely examples and other suitable configurations of the pressure sensors P1, P2 may be implemented to measure the pressure of the fluid in the channel 150.

The pressure of the flowing fluid and resistance(s) of the channel 150 may be used to determine various parameters to evaluate a patient's usage of the nebulizer and adaptor 10. One such parameter is the volumetric flow rate. This is the volume of fluid flowing through the adaptor 10 at a given point in time Analysis of the volumetric flow rate over time may indicate the amount of medication, e.g., volume, inhaled by a patient using the adaptor 10 with a nebulizer.

The volumetric flow rate may be determined based on a first pressure detected by pressure sensor P1, a second pressure detected by pressure sensor P2, and the resistance of the channel in between the locations of the two sensors P1 and P2. The resistance may be the value R2 in the second channel region 154. The pressures may correspond to measurements made with the sensors P1 and P2 in, respectively, the first and third channel regions 152 and 156. Such measurements may be used to calculate the volumetric flow rate based on the type of flow through the channel 150. For laminar flow, the volumetric flow rate "Q" may be determined from the following equation: P2−P1=R2×Q. For turbulent flow, the volumetric flow rate "Q" may be determined from the following equation: P2−P1=R2×Q2+R2×Q. The values for "Q" over time may be plotted and analyzed to determine the quantity and frequency of breaths, or the duration and volume of breathing, as detected by the sensor(s) (e.g., mass airflow sensor and/or pressure sensor) of the adaptor 10, as further described herein, for example with respect to FIGS. 13 and 14.

Figure 5:
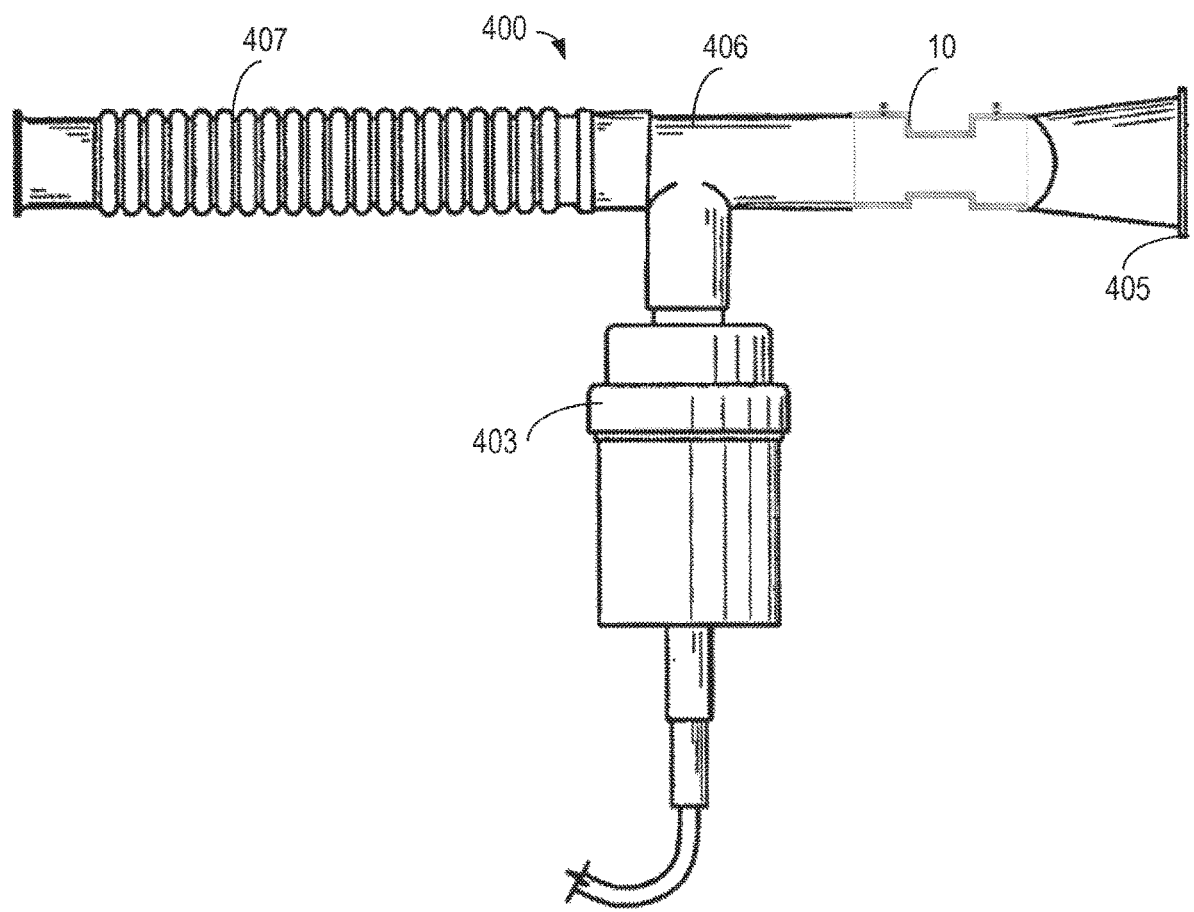
FIG. 5 is a side view of a mouthpiece nebulizer with the nebulizer adaptor of FIG. 4.

FIG. 5 illustrates an example of the nebulizer adaptor 10 with a mouthpiece nebulizer 400. The nebulizer adaptor 10 may be removable from the mouthpiece nebulizer 400 as desired in various examples. In the example depicted in FIG. 5, the nebulizer adaptor 10 is positioned between a T-piece 406 and a medication distribution end 405 of the mouthpiece nebulizer 400. In additional or alternative embodiments, the nebulizer adaptor 10 is positioned between a medication source 403 and a T-piece 406, in additional or alternative embodiments, the nebulizer adaptor 10 is positioned between a T-piece 406 and a corrugated reservoir tube 407. In various other examples, the adaptor 10 may be used with various other types of nebulizer accessories. In various examples, the nebulizer adaptor 10 can Include sensors that sense a fluctuation in temperature, pressure, or other physical attributes, alone or in combination. In some embodiments, the adaptor 10 may calculate volumetric air flow based on the fluctuation in temperature and/or pressure. In additional or alternative embodiments, the adaptor 10 may determine a direction and magnitude of fluid flow through the adaptor 10.

Figure 6:
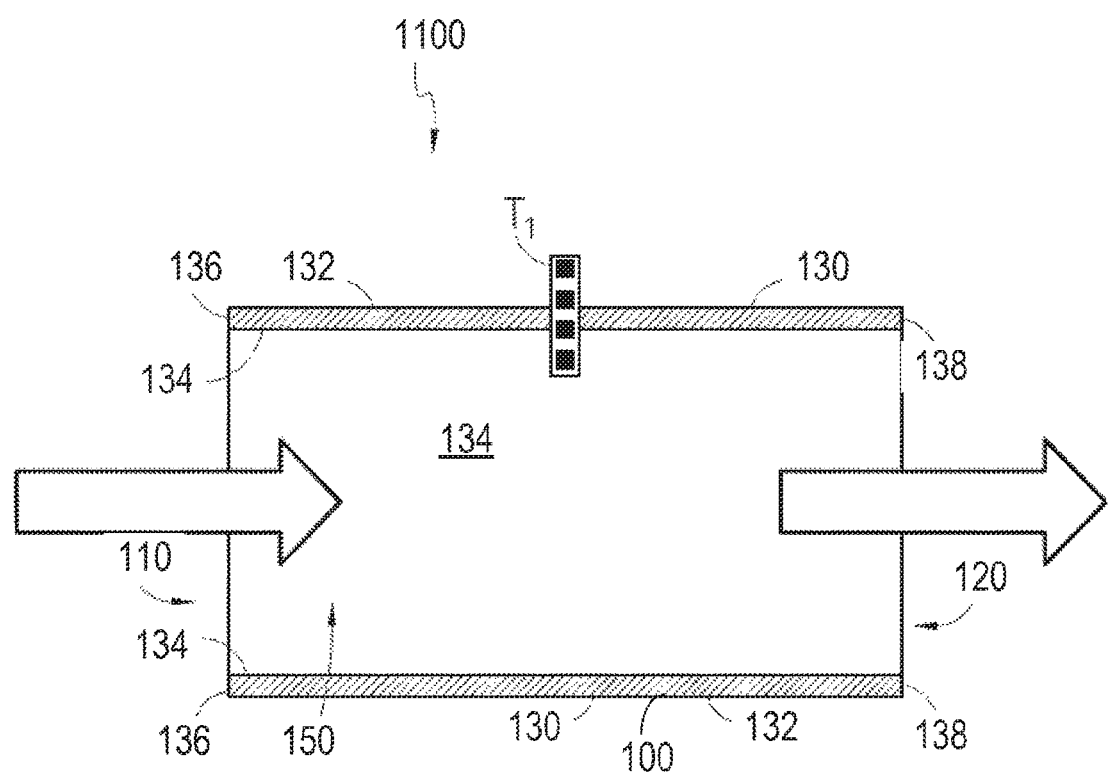
FIG. 6 is a sectional view of another embodiment of a nebulizer adaptor.

FIG. 6 is a cross-section view of another embodiment a nebulizer adaptor 1100. The nebulizer adaptor 1100 may be substantially similar to the nebulizer adaptor 10. For example, the body 100 in FIG. 6 may have the same or similar features and/or functionalities as the body 100 described with respect to FIG. 4, and vice versa, except as noted or where context indicates otherwise.

As shown in FIG. 6, a portion of the adaptor 1100 is shown, including portions of the body 100, first opening 110, the second opening 120, the sidewall 130, the outer portion 132, the inner portion 134, the first edge 136, the second edge 138 and the channel 150. The sidewall 130, for example the outer portion 132, the inner portion 134, the first edge 136, and/or the second edge 133, may extend generally along the shown contour along the sides of the adaptor 1100 from the first opening 110 to the second opening 112. Fluid may flow through the channel 150. The fluid may flow through the channel 150 in the direction indicated by the arrows in FIG. 4, which may indicate an inspiration by a patient using a nebulizer with the adaptor 1100. Expirations may be in the opposite direction as that indicated by the arrows.

The channel 150 may have a geometry along the direction of fluid flow that is the same or similar as any of the regions 152, 154, 156 described with respect to FIG. 4. For instance, the channel 150 may have a geometry (e.g. a width, cross-sectional area, etc.) that is similar to that of one or more of the openings 110, 120. The geometry of the channel 150 along the direction of flow may be generally uniform. In some embodiments, the geometry of the channel 150 may vary.

The adaptor 1100 of FIG. 6 may have one or more sensors, such as one or more of the sensors 210, 212. As shown, the adaptor 1100 may have a temperature sensor T1. The temperature sensor T1 may have the same or similar features and/or functionalities as the sensors 210, 212. The temperature sensor T1 may be part of the system 200. The temperature sensor T1 and other components of the system 200 may be coupled with the body 100 of the adaptor 1100.

The temperature sensor T1 may detect the temperature of the fluid flowing through the channel 150. As shown, the temperature sensor T1 may be located in the adaptor 1100 to detect the temperature along the channel 150 at a location generally midway between the first and second openings 110, 120. The temperature sensor T1 may be in other locations.

Additional temperature sensors may also be positioned in these or other locations of the channel 150. Thus, the configuration shown is merely an example and other configurations may be implemented.

The temperature sensor T1 may protrude into the channel 150 through an opening in the body 100 (not shown). In some embodiments, there may be an opening in the body 100 and the temperature sensor T1 may be adjacent the opening, but not protrude into the channel 150. These are merely examples and other suitable configurations of the temperature sensor T1 may be implemented to measure the temperature of the fluid in the channel 150.

The temperature of the flowing fluid may be used to determine various parameters to evaluate a patient's usage of the nebulizer and adaptor 1100. One such parameter is the direction of flow of the fluid. Flow in the direction indicated in FIG. 6 may indicate inspiration, while flow in the opposite direction may indicate expiration. Analysis of the direction of flow over time may indicate one or more of the quantity and the frequency of breathing, as detected by one or more sensors (e.g., flow sensor, pressure sensor, temperature sensor, etc.) of the adaptor 1100, by a patient using the adaptor 1100 with a nebulizer.

The direction of flow may be determined based on a first temperature detected by the temperature sensor T1 and a second temperature detected by the temperature sensor T1. The detected temperatures may be detected at different points in time. The differences in the detected temperatures may indicate the direction of fluid flow through the channel 150. For example, a temperature detected that is about the same as room temperature may indicate an inspiration, and a temperature detected that is about the same as a human body temperature may indicate an expiration. In some cases, the temperature indicative of an expiration will be greater than the temperature indicative of an inspiration. However, ambient temperatures may be sufficiently high such that the mom temperature is higher than normal.

In some embodiments, the temperature sensor T1 may also detect the temperature in the channel 150 before fluid begins flowing through the channel 150, in order to establish the room temperature. The differences. In the detected temperatures may be analyzed over time to determine one or more of the quantity and the frequency of breaths or duration of breathing taken with the adaptor 1100 and a nebulizer, as described in further detail herein, for example with respect to FIGS. 13 and 14.

In some embodiments, the adaptor 1100 may include both pressure and temperature detections. For instance, the adaptor 1100 may include both pressure sensors and temperature sensors, such as pressure sensors P1 and P2 and temperature sensor T1. This may provide for a more reliable assessment of the use of the adaptor 1100 with a nebulizer.

Figure 7:
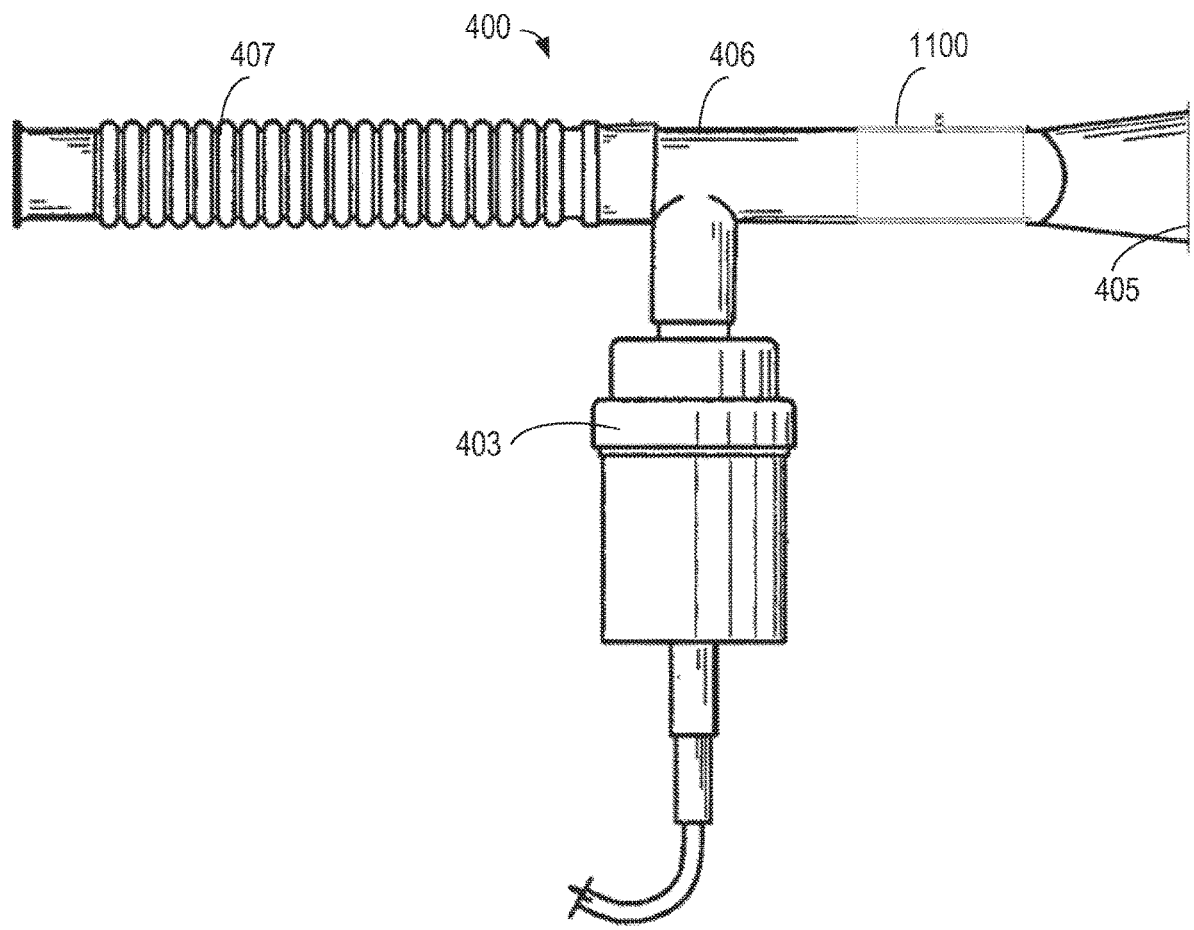
FIG. 7 is a side view of a mouthpiece nebulizer with the nebulizer adaptor of FIG. 6.

FIG. 7 illustrates an example of the nebulizer adaptor 1100 with the mouthpiece nebulizer 400. The nebulizer adaptor 1100 may be removable from the nebulizer 400 as desired. In various embodiments, the adaptor 1100 may be used with various other types of nebulizer accessories. In various embodiments, the nebulizer adaptor 1100 can calculate a magnitude of a fluid flowing through the adaptor by including sensors configured to sense a fluctuation in magnitude of one or more physical attribute such as temperature, pressure, carbon dioxide, etc.

Figure 8:
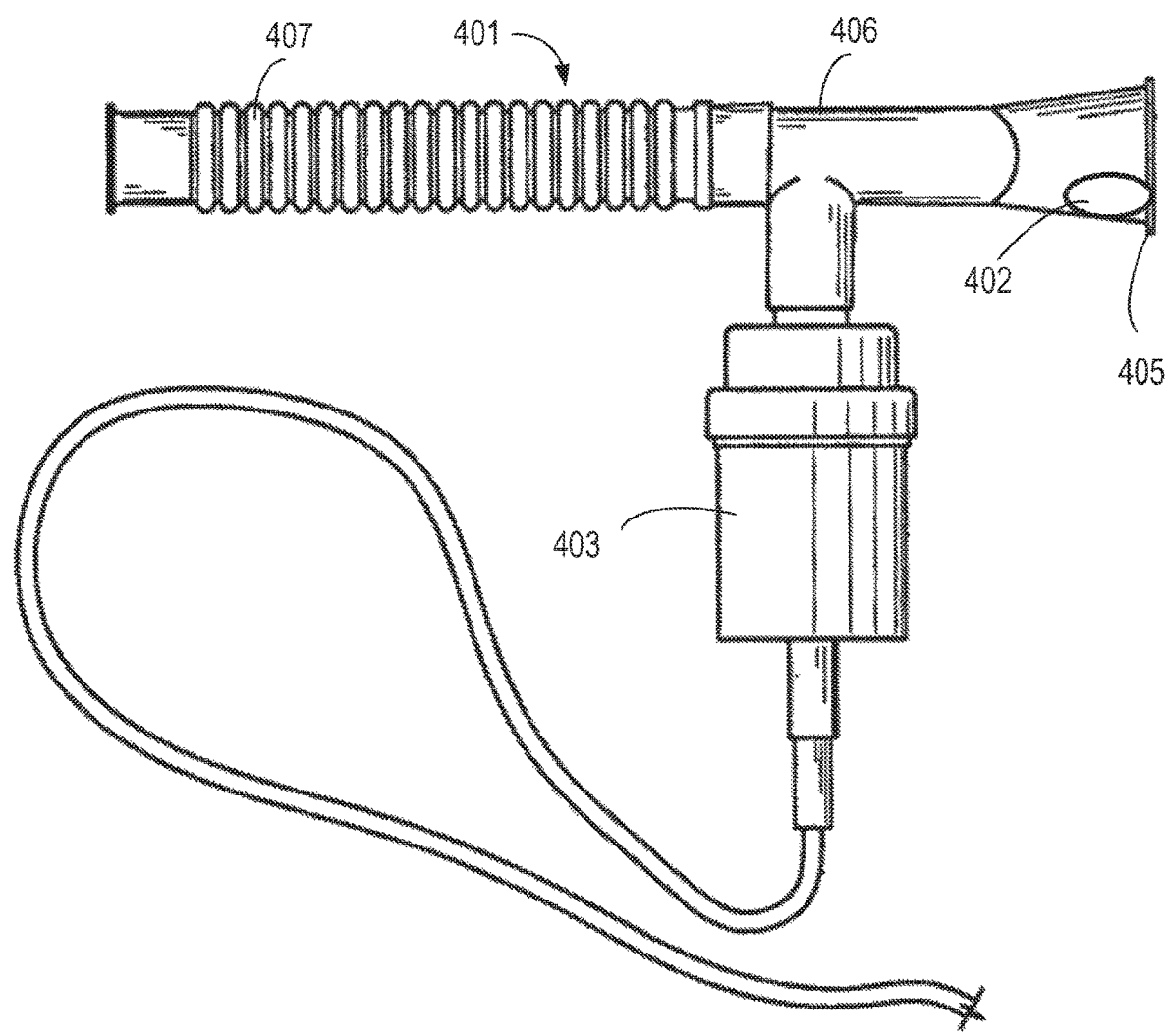
FIG. 8 is a sectional view of another embodiment of a mouthpiece nebulizer.

FIG. 8 is another example of a mouthpiece nebulizer 401 as a nebulizer accessory. In this example, the mouthpiece nebulizer 401 includes a capacitive touch sensor 402. The capacitive touch sensor 402 can detect and determine if the mouthpiece nebulizer 401 is proximate to a user, as well as changes in proximity of the user to the mouthpiece nebulizer 401. The location of the touch sensor 402 on the mouthpiece nebulizer 401 is presented for illustrative purposes, but other implementations are possible. In other embodiments, the touch sensor 402 may be placed at various locations on the mouthpiece nebulizer 401 to detect touch or proximity of a user to the mouthpiece nebulizer 401. In various examples, the touch sensor 402 may be tuned and configured to detect that the patient is within a predetermined distance (e.g. 12 inches, less than 12 inches away, greater than 12 inches away, etc.) from the nebulizer accessory. In some examples, the touch sensor 402 may detect the presence of the patient without the patient touching the mouthpiece nebulizer 401. In other examples, the touch sensor 402 may ultimately detect that the nebulizer accessory 401 is within the user's mouth or near the face of the user.

Figure 9:
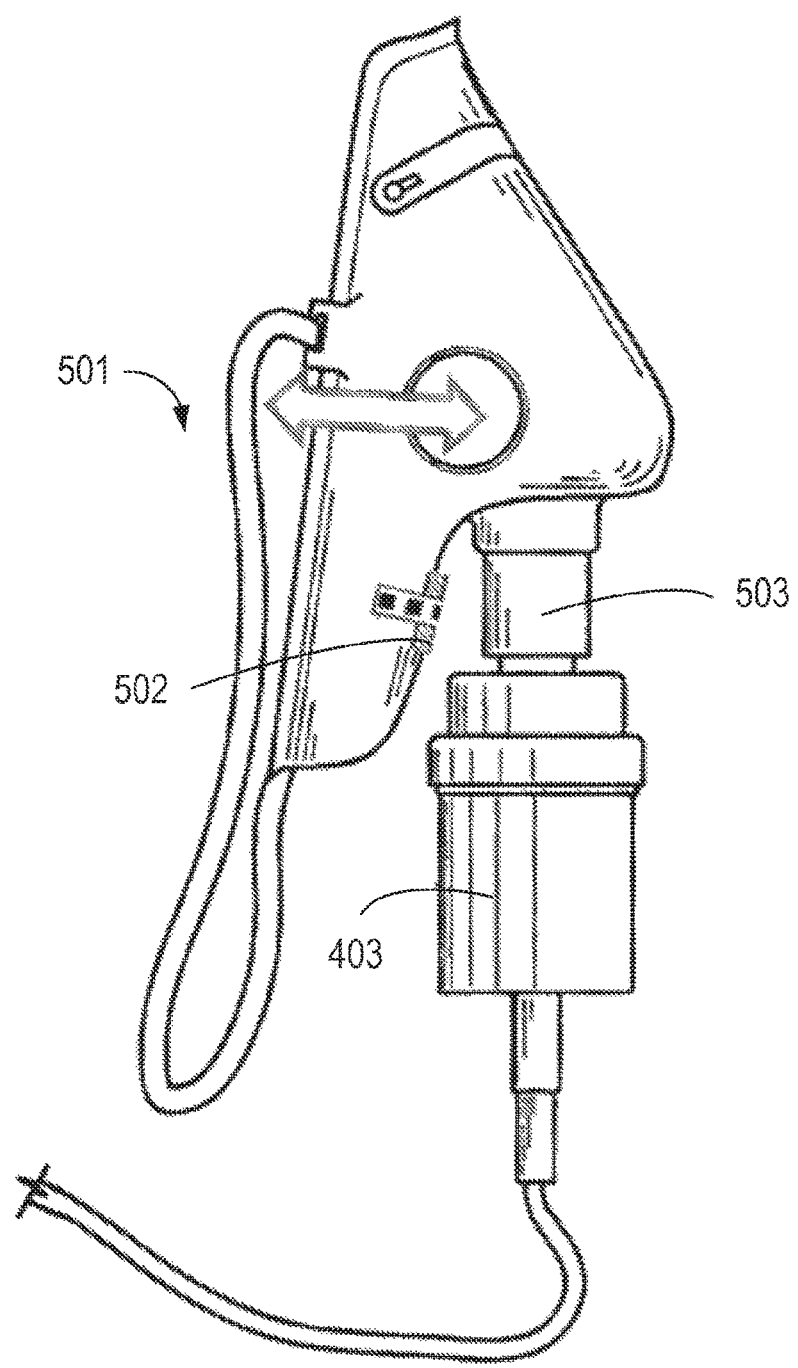
FIG. 9 is a sectional view of another embodiment of a nebulizer mask.

FIG. 9 is an example of a mask 501 as a nebulizer accessory. The mask 501 includes a sensor 502. In some examples, the mask 501 is connected to the medication source 403 through an adaptor 503. In various examples, the sensor 502 may be removable from the mask 501 or may be fixedly attached to the mask 501. In some embodiments, an opening may be defined by the mask 501 that is sized and configured to receive the sensor 502. In other examples, an opening for the sensor 502 may be omitted. The sensor 502 is similar to the sensor of the nebulizer adaptor 1100 (see FIG. 5) and can sense a fluctuation in one or more physical attributes such as temperature, pressure, carbon dioxide, etc. Similar to the nebulizer adaptor 1100, the sensor 502 and mask 501 may calculate air flow based on the fluctuation in one or more of temperature, carbon dioxide, and pressure.

Figure 10:
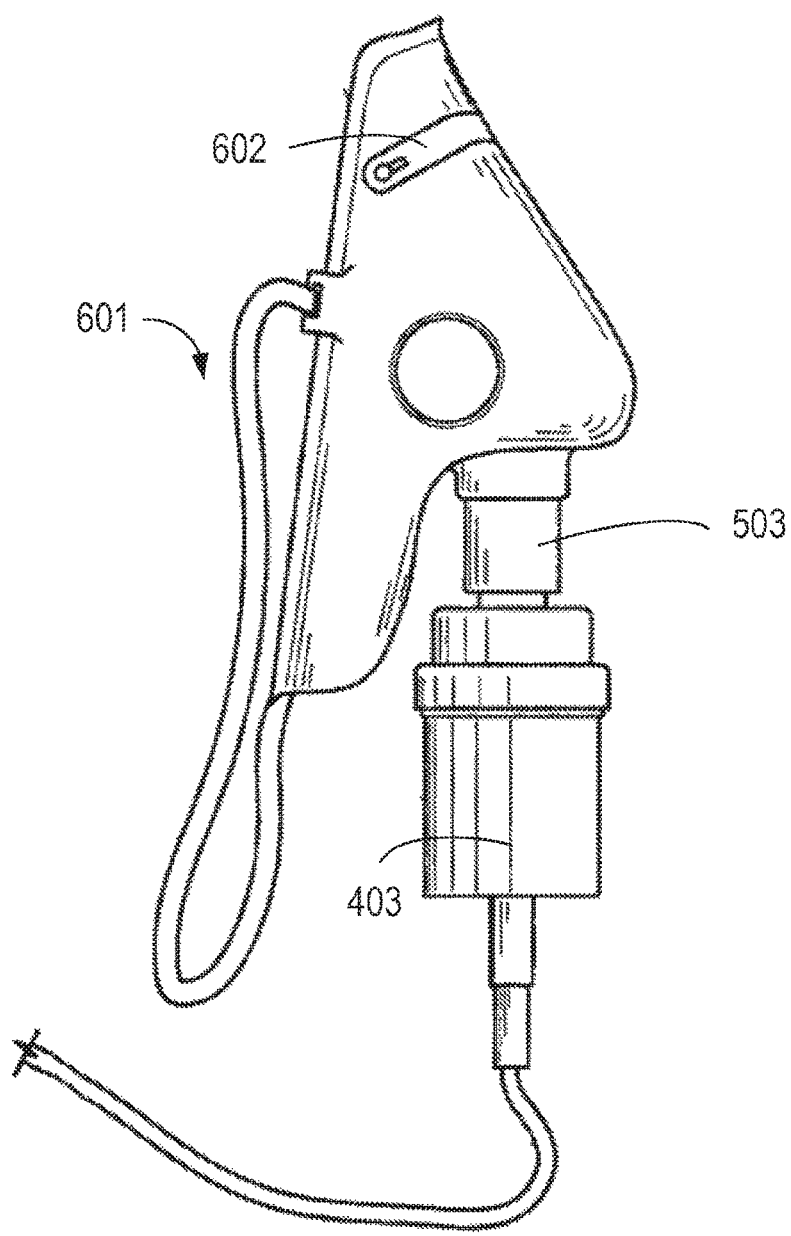
FIG. 10 is a side view of an embodiment of a nebulizer mask.

FIG. 10 is an example of a mask 601 with a capacitive touch sensor 602, which may be substantially similar to the touch sensor 402 of the nebulizer accessory 401. The location of the touch sensor 602 on the mask is depicted for illustrative purposes, but other implementation is possible. In various embodiments, the touch sensor 602 may be placed at various locations on the mask 801 to detect touch or proximity of a user to the mask 601.

Figure 11:
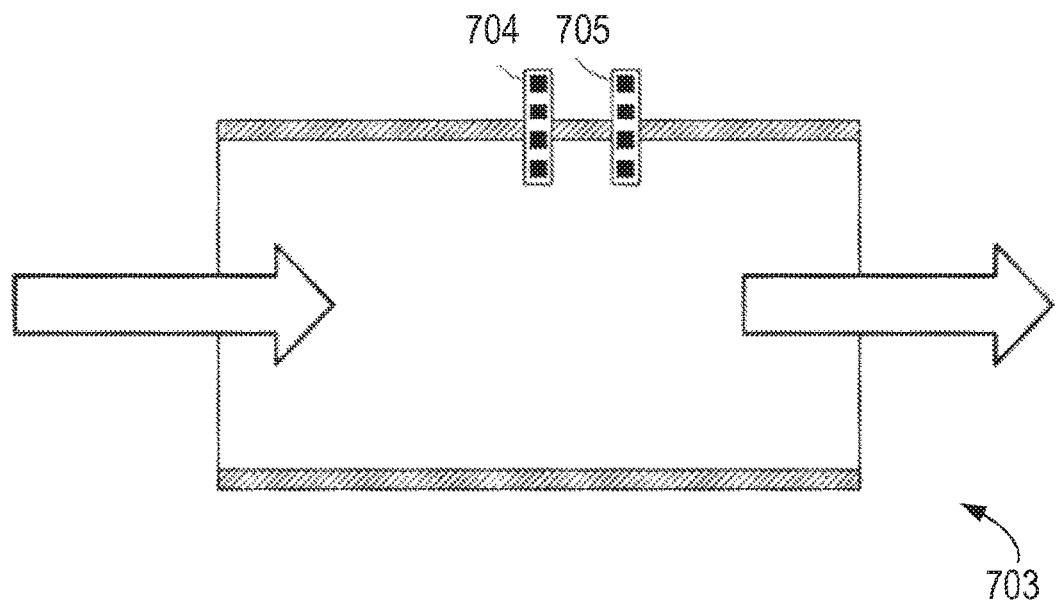
FIG. 11 is a sectional view of an embodiment of a nebulizer adaptor.

FIG. 11 is an example of an adaptor 703 that may be used with the mask 501 or 601 in place of the adaptor 503 or with the mouthpiece nebulizer 400 or 401 between the nebulizer 403 and the T-piece 406 or with the mouthpiece nebulizer 400 or 401 between the T-piece 406 and the medication distribution end 405. In other examples, the adaptor 703 may be used with a standard nebulizer mask. The adaptor 703 is similar to the adaptor 1100. In the example depicted in FIG. 11, the adaptor 703 includes two physical attribute sensors 704 and 705 that can detect a change in humidity through the adaptor 703 and user's proximity to the adaptor 703, respectively.

Figure 12:
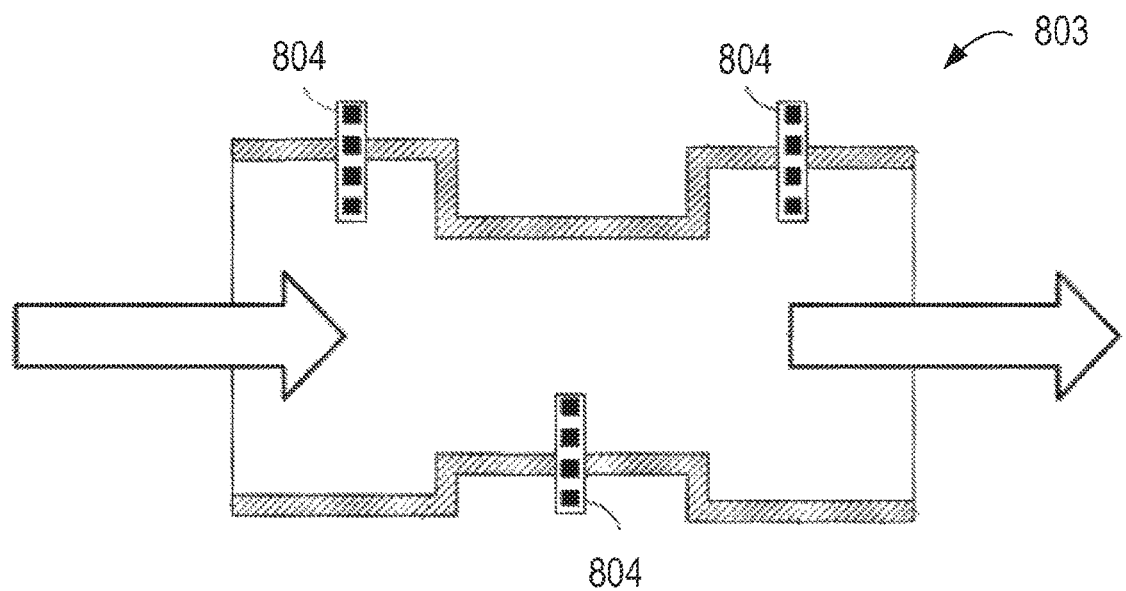
FIG. 12 is a sectional view of another embodiment of a nebulizer adaptor.

FIG. 12 is another example of an adaptor 803 that may be used with the mask 501 or 601 in place of the adaptor 503. In some embodiments, the adaptor 803 may be used with a standard nebulizer mask. In the example depicted in FIG. 12, the adaptor 803 includes two physical attribute sensors 804 that can detect a change temperature and/or pressure and one physical attribute sensor 805 that can detect touch or proximity to a user. However, as with the other nebulizer therapy accessories such as the nebulizer adaptors, mouthpieces, or masks, the number or type of physical attribute sensors 804 should not be considered limiting on the present disclosure.

Figure 13:
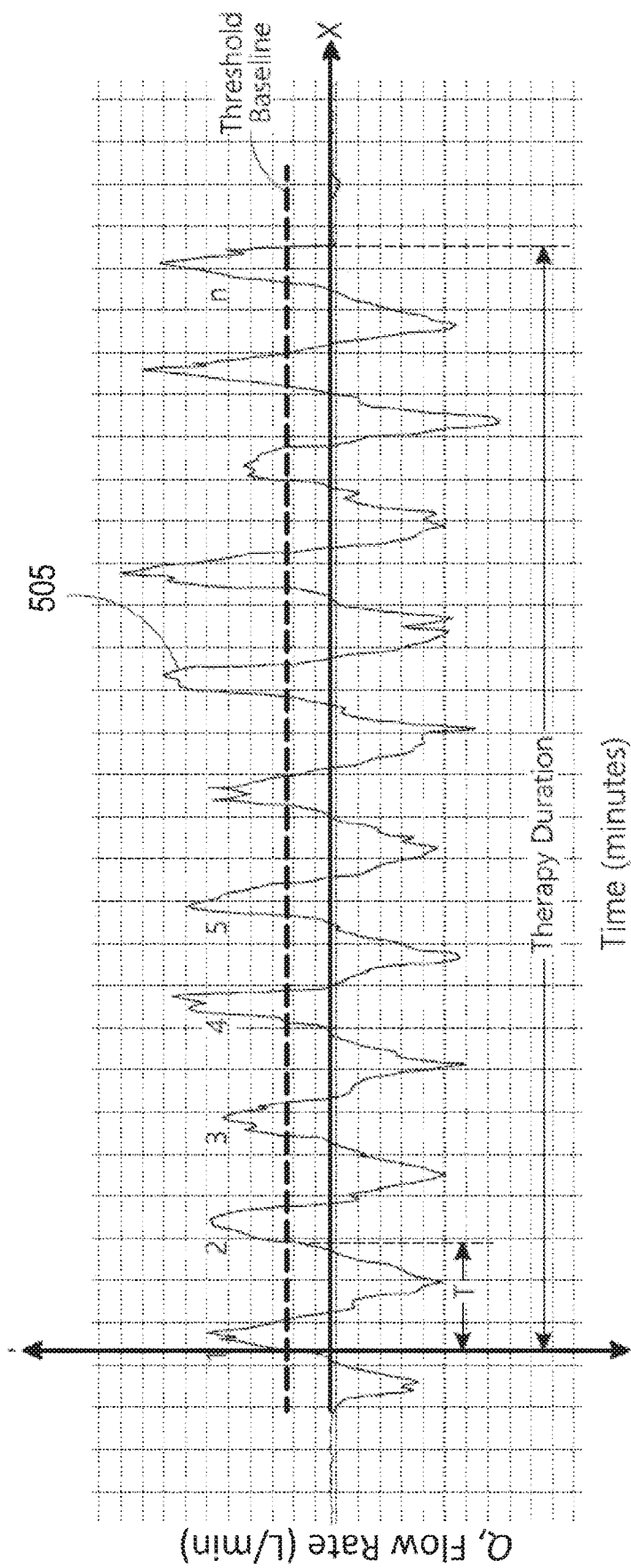
FIG. 13 is a sample data plot showing example of data, generated with the various nebulizer adaptors described herein, that can be used to produce a compliance score indicative of the patient's compliance with the nebulizer therapy.
Figure 14:
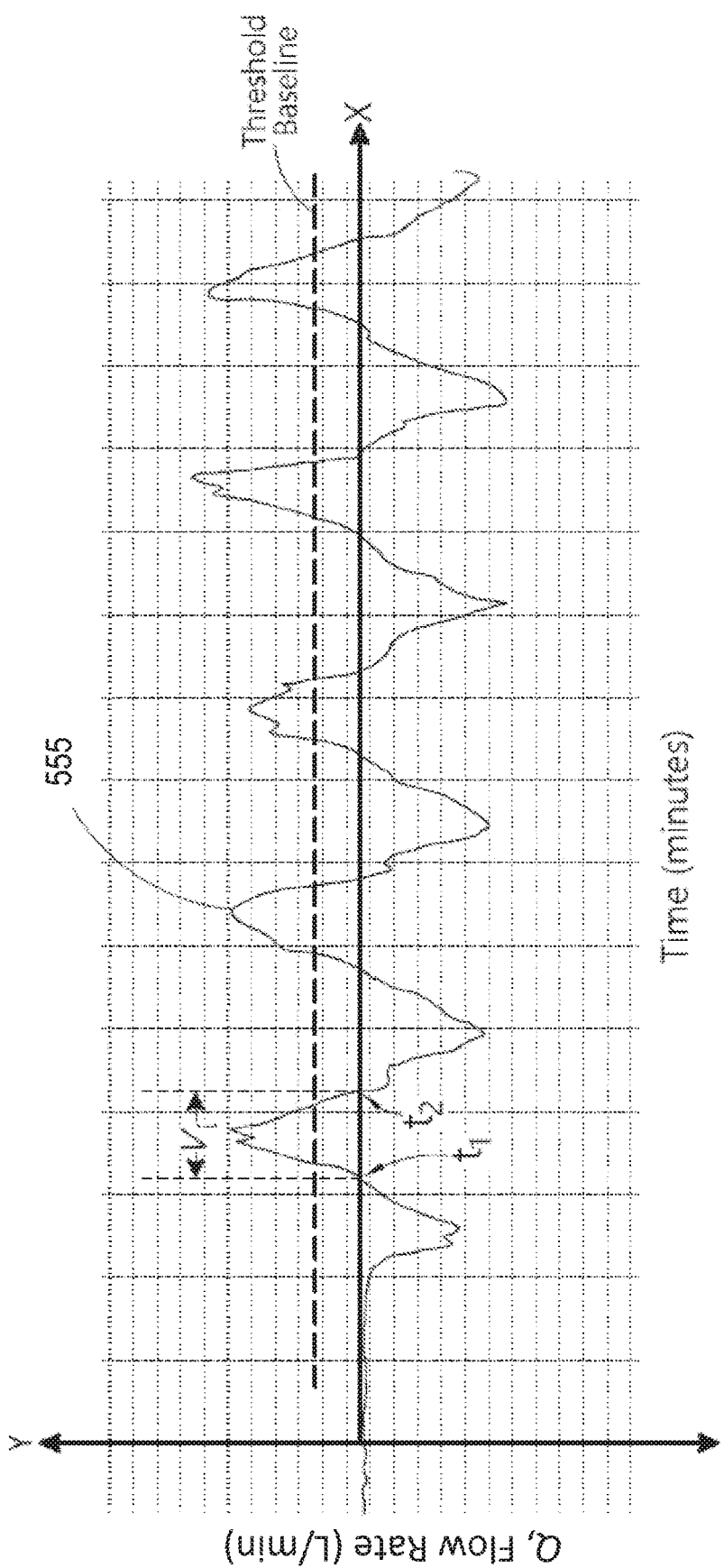
FIG. 14 is another sample data plot showing example of data, generated with the various nebulizer adaptors described herein, that can be used to produce a compliance score indicative of the patient's compliance with the nebulizer therapy.

FIGS. 13-14 are sample data plots showing examples of flow data, generated with the various nebulizer adaptors described herein, that can be used to produce an indicator of the compliance with use of the nebulizer. The various plots may be produced from using the adaptor 10 with a nebulizer, as described herein. The data may be produced by the system 200 by detecting the various physical attributes of the fluid flow and/or user touch or proximity to the user. The data may be collected using one or more of the sensors 210, 212. The various calculations of the data may be performed by the processor 220. The data may be stored in the system 200, such as in the memory 240. In some embodiments, the data may be communicated using the communication circuit 250 to a separate device, such as a dedicated device, hub, or mobile device, as described herein. In some embodiments, the processor 220 can analyze the data to calculate an indicator of the compliance with the nebulizer. The indicator may be communicated using the communication circuit 250 to separate devices, as described herein.

FIG. 13 depicts a plot 500 of data 505 of the volumetric flow rate "Q" on the Y-axis versus time on the X-axis. In some embodiments, the Y-axis may be the voltage produced by a pressure, humidity, carbon dioxide, or temperature sensor in response to detecting pressure, humidity, carbon dioxide, or temperature, respectively. The plotted data 505 is cyclical, with various peaks and valleys. Five of the peaks are numbered 1-5, with the last peak labeled generically as "n."

The data 505 in plot 500 can be used to calculate one or more of the quantity and the frequency of breathing. Portions of the data 505 above the X-axis indicate a positive value for volumetric flow rate (or voltage), while pardons of the data 505 below the X-axis indicate a negative value for volumetric flow rate (or voltage). The positive values (above the X-axis) may indicate flow m a first direction through the adaptor 10 (e.g., inspiration), while the negative values (below the X-axis) may indicate flow in a second direction through the adaptor 10 (e.g., expiration) that is opposite the first direction.

To account for noise or artifacts in the data 505, one or more thresholds may be used. As shown in FIG. 13, a baseline threshold for positive data may be determined. The baseline threshold may be a positive lima above which the data 505 must reach in order to be counted as a breath (e.g., an inspiration). In some embodiments, a second baseline (not shown) may be determined for negative data. This negative threshold may be a negative limit below which the data 505 must reach in order to be counted as a breath (e.g., an expiration). The values for the various thresholds may be determined based on experimentation and aspects of the particular sensors and equipment used, such as sensor resolution. As shown, the first five peaks 1-5 all extend above the baseline threshold, and thus these are indicative of five inspirations. Similar analyses may be done ail the way out to the "nth" peak.

The breathing frequency may be determined by the period "T" as indicated in the data 505. The period T is the time in between consecutive crossings of the same value on the Y-axis. For instance, the period T as shown may be determined based on the time in between consecutive crossings of the baseline threshold. For example and without limitation, the consecutive crossings of the baseline threshold may be based on the time between consecutive inhalations crossing the baseline threshold value, consecutive exhalations crossing the baseline threshold value, an inhalation and an exhalation crossing the baseline threshold value, various combinations thereof, and venous other crossings of the baseline threshold. The breathing frequency, f, in breaths per minute, is determined by the period, T of the breathing waveform with the following equation: $f=1/T$.

The data 505 in plot 500 can be used to calculate the duration of the breathing therapy. This may be the time indicated in FIG. 13 as "Therapy Duration." The duration of therapy may be the total time from when the first inspiration crosses the baseline threshold and the last inspiration crosses the baseline threshold. The duration of therapy may be determined by a component of the system, such as the adaptor 10, relay communication device, hub, or mobile device. Various other components of the system may be used in place of or in addition to the adaptor 10 to determine the duration of therapy. In some embodiments, the adaptor 10 or other system component records a timestamp at the time at which the first inspiration crosses the baseline threshold and a treatment timer is started. Use of the baseline threshold may account for noise or artifacts in the data, as mentioned.

Although reference wilt now be made to the adaptor 10, it will be appreciated that the following actions may be performed by other components of the system, such as the relay communication device, hub, or mobile device, or other components, either in conjunction with the adaptor 10 or in place of the adaptor 10. In some embodiments, the adaptor 10 determines duration based on the times corresponding to when the first and last inspirations cross the X-axis. The adaptor 10 may also use and record other beginning and end times. For example, the second or third crossing may be used to indicate the beginning, in order to account for startup irregularities, a pause of breathing, and the like. Similarly, the second- or third-to-last crossing may be used to indicate the ending, to account for ending irregularities and the like.

As another example, the adaptor 10 may use a time between consecutive crossings of the baseline threshold to determine a pause of breathing during the breathing therapy. In some cases, the adaptor 10 may use the pause of breathing to calculate the duration of the breathing therapy. In these examples, the adaptor 10 records a timestamp at the time at which a first inspiration crosses a baseline threshold and starts a treatment timer. The adaptor 10 may also record treatment timestamps for subsequent baseline threshold crossings by the air flow signal. The adaptor 10 determines a pause of breathing by (i) measuring the time period measured from a previous treatment timestamp to the current time on the timer, and (ii) comparing that time period with a pre-determined pause value. If, during the therapy session, adaptor 10 determines that the time period measured exceeds the pre-determined pause value, such as 15 seconds or various other time periods, the adaptor 10 may pause the timer. The adaptor 10 may resume the timer if the adaptor 10 determines (i) a subsequent baseline threshold crossing is determined and (ii) that the time period does not exceed a timeout value. If the adaptor 10 resumes the timer, the adaptor records the time period from the previous treatment timestamp to the timestamp of the subsequent baseline threshold crossing as a pause duration.

In some cases, if the adaptor 10 does not determine a subsequent baseline threshold crossing and further determines that the time period exceeds the predetermined timeout value, such as 8 minutes or various other time periods, the adaptor 10 records and marks the previous treatment timestamp as an end timestamp. The adaptor 10 records the time period from the start timestamp to the end timestamp as the treatment duration. To determine an actual treatment duration, the adaptor 10 may modify the treatment duration by subtracting the pause duration from the treatment duration. In some cases, the adaptor 10 determines a compliance score by comparing the actual treatment duration to an expected treatment duration. The expected treatment duration may be pre-determined and may be received by a device from a user, although it need not be.

These are merely examples and other crossings based on various criteria may be used to define the beginning and ending of a therapy session.

FIG. 14 depicts a plot 550 of data 555 of the volumetric flow rate "Q" on the Y-axis versus time on the X-axis. The data 555 in plot 550 can be used to calculate the volume of therapeutic breaths. The following calculations may also be performed on the data 505 of the plot 500. Similarly, the calculations described with respect to FIG. 13 can be performed on the data 555 of the plot 550. Further, the same or similar features of the data 505 in FIG. 13 may be used with the data 555 in FIG. 14. For instance, positive and negative values may be above and below the X-axis, one or more thresholds may be used, crossings of the thresholds and/or X-axis may be used for various beginning and endpoints of the therapy and to make various calculations, etc.

The data 555 in plot 550 can be used to calculate the inhaled volume for a given breath and/or total inhaled volume for a given therapy session. As shown, a first volume of inhaled breath Vi may be calculated based on data associated with the indicated peak. The data associated with the indicated peak crosses the threshold in two places. This may be used to determine that this portion of the data is a viable candidate for calculating the inhaled volume of that breath. The times at which the data associated with that peak crosses the X-axis may be indicated as t1 and t2. The value t1 may be a first time at which the data first crosses the X-axis from negative to positive values, and the value t2 may be a second time at which the data next crosses the X-axis from positive to negative values. Thus, the time from t1 to t2 may indicate the total time of inspiration for that breath. The volume of inhaled breath Vi can be calculated by adding the area underneath the indicated peak from t1 to t2. This may be done for example by making the following mathematical integration of the data 505, with t1 as the lower limit of integration and t2 as the upper limit of integration: $Vi=\int Q\ dt$. Similar calculations can be done for the other peaks in the data 555. Thus, a series of volumes for individual breaths may be determined in this manner. The series of individual volumes may be added to determine the total volume for the entire therapy session.

The calculated quantity, frequency, volume and/or duration of therapy may be used to calculate an indicator of a compliance with the therapy. For instance, the normal lower limit of breathing for an adult may be used, e.g., eight breaths per minute. Further, an absolute lower limit may be used based on this lower limit, e.g., five breaths per minute. In some embodiments, if the frequency of drops below the absolute lower limit, e.g., five breaths per minute, for a predetermined period of time and/or a predetermined number of breaths, the indicator of compliance may be adjusted lower. In some embodiments, the event may be flagged and used to adjust the compliance indicator. For instance, the indicator may be 100% for a perfect therapy session, and a drop under the limit for the predetermined time or number of breaths may lower that percentage, e.g., to 75% or some other value, depending on the amount of the difference from a normal breathing frequency and/or the duration of the difference.

As a further example, if the total therapy time is ten minutes, then a required breath count may be greater than fifty. Thus, if the breath count is slightly less than fifty, then the indicator may be adjusted slightly downward. If the breath count is much less than fifty, then the indicator may be adjusted relatively further downward.

As further example, if a patient is supposed to use the nebulizer for a given amount of time every day, the total duration of therapy may be used to generate the indicator of compliance. For instance, a patient may be required to use the nebulizer for twenty minutes a day. If the total determined duration of therapy is less than twenty minutes for a given day, then the indicator of compliance may be adjusted downward. In this manner, compliance and adherence to prescribed medication regimens may be monitored.

As further example, even if the frequency and duration are acceptable, i.e. of high "compliance," other parameters may be used to further assess the therapy. For instance, the frequency may be high enough, but the volume may not be adequate if, for example, the breaths were too short or not deep enough. Thus, the volume per breath and/or total volume may supplement other calculations used to determine the indicator of compliance. In some embodiments, the volume per breath or total volume may be used alone (e.g., without frequency or duration data) to determine the frequency. Regardless of how the volume per breath is used, the volume calculations may be determined based on a selected normal inspiration volume, i.e. a tidal volume. For instance, this may be determined to be fifty milliliters (ml). This number may be different for different patients, e.g., based on age, fitness, etc. An absolute limit may be based on the normal volume, e.g., forty-five milliliters (ml). If the calculated volume per breath Vi drops below the normal amount (or absolute limit), then the indicator may be adjusted downward accordingly. In some embodiments, the event may be flagged and used to adjust the compliance indicator. For instance, the indicator may be 100% for a perfect therapy session, and a drop under the limit for a given breath and/or therapy session may lower that percentage, e.g., to 75%, or some other value, depending on the amount of the difference from a normal or selected tidal volume and/or the duration of the difference.

In some embodiments, more than one flow attribute may be used to calculate the indicator of compliance. For example, both pressure and temperature flow data may be used by a single adaptor 10 having both pressure and temperature sensors or sensing capabilities, in order to calculate the indicator.

These are merely some examples of how the indicator of compliance may be determined, and various other calculations or variations thereof may be used based on the discrepancy with the normal or expected/selected breathing characteristics during the therapy. The adaptor 10 may itself make such calculations, or it may communicate the raw data to another device that may then make such calculations. Regardless, the resulting indicator of compliance may be communicated to various interested parties, as described herein.

Figure 15:
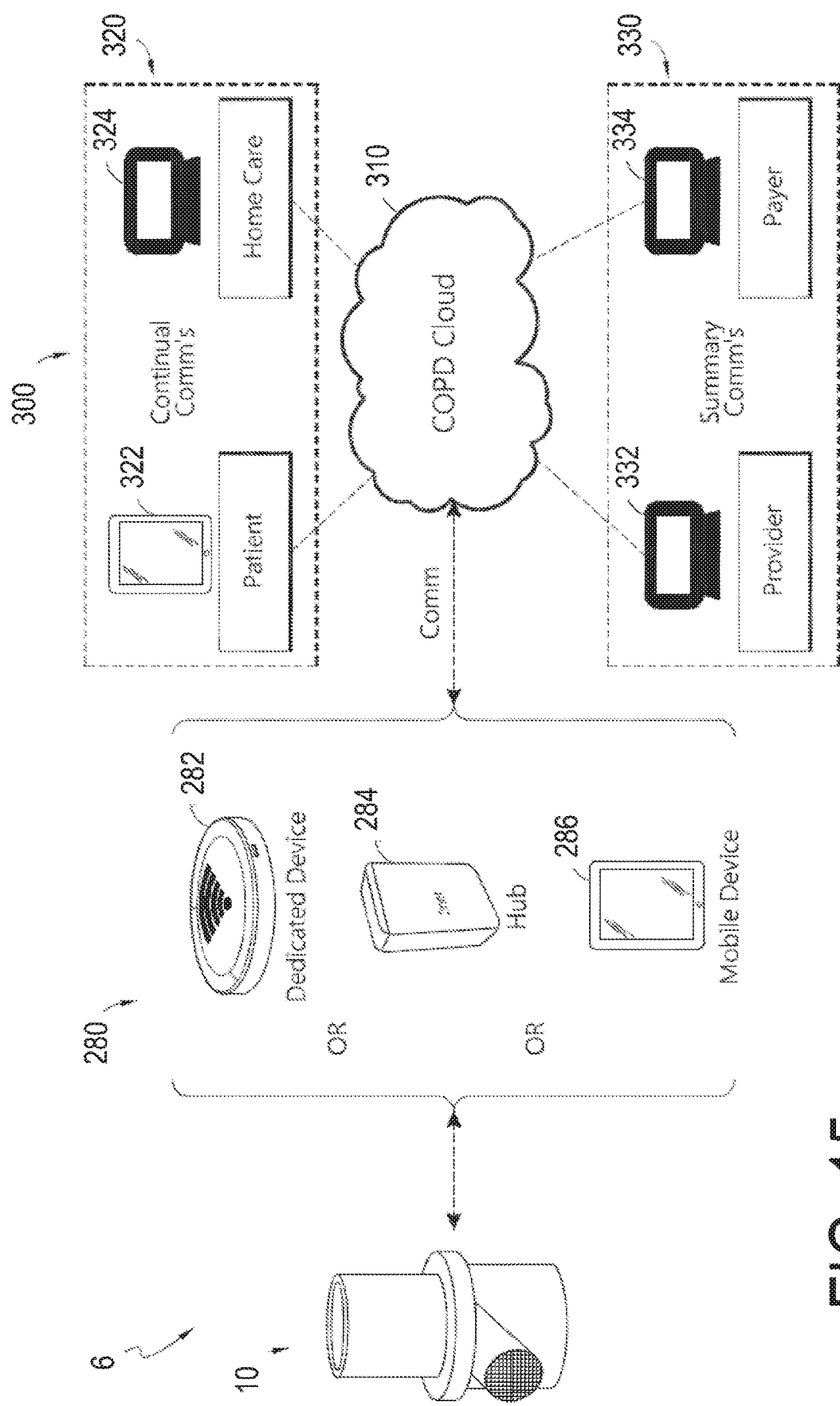
FIG. 15 is a schematic of an embodiment of a system that includes the nebulizer adaptor of FIG. 1, a receiving device and a network.
Figure 16:
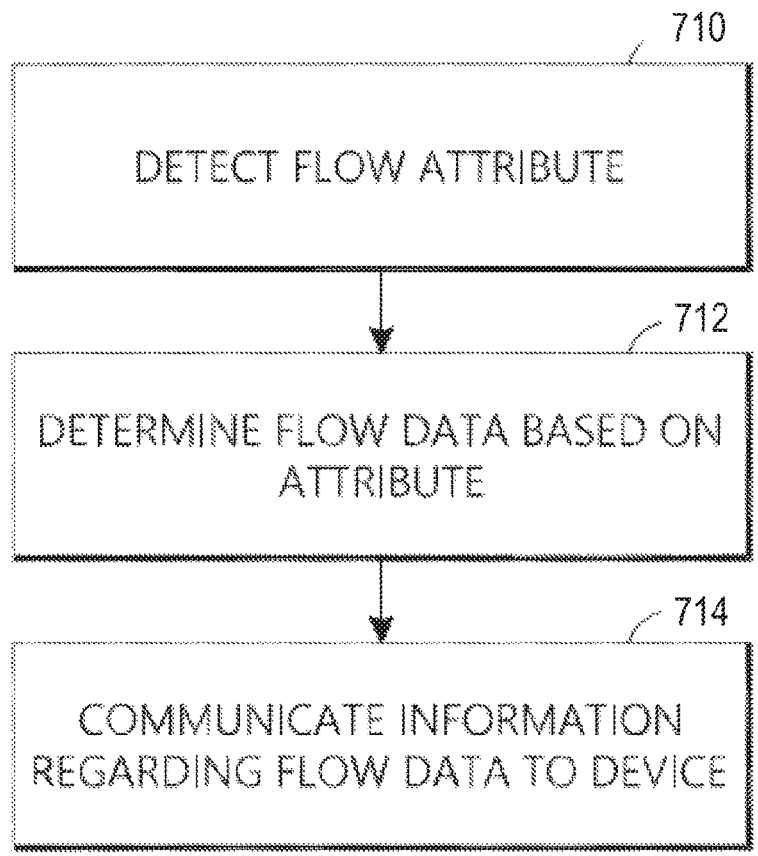
FIG. 16 is a flowchart showing an embodiment of a method for using the various nebulizer adaptors described herein to assess nebulizer therapy.

FIG. 15 is a schematic of an embodiment of a system 6 that includes the nebulizer adaptor 10, a receiving relay communication device 260 and a network 300. The adaptor 10 (e.g., the electronics system 200) may be in data communication with the relay communication device 280. This communication may be via Bluetooth or other near field communication protocols (NFC), and may be wired or wireless. The relay communication device 280 may be in data communication with the network 300 (e.g., using the internet, using cedar data, etc.). In some embodiments, additionally or alternatively to being in data communication with the relay communication device 280, the adaptor 10 may be in data communication directly with the network 300. The various communication connections may support secure socket layer (SSL) communication or encryption of data.

The relay communication device 280 may be any of a number of electronic devices capable of communicating with the adaptor 10. The relay communication device 280 may be a receiving device 282. The receiving device 282 may be dedicated to communicating with the adaptor 10. Thus, the receiving device 282 may be optimized to communicate with the adaptor 10 and to provide communications, alerts, etc. to the patient using the adaptor 10. In various examples, the receiving device 282 is capable with communicating with any of the aforementioned nebulizer therapy accessories (adaptors, mouthpieces, and/or masks). In various examples, the receiving device 282 is capable of communicating with the nebulizer therapy accessory with a short range communication protocol. In some examples, communication with the receiving device 282 may be wired or wireless communication. The receiving device 282 may further be capable of communicating over a cellular network. In some embodiments, the receiving device 282 may provide wireless charging to the power source of the adaptor 10. For example, the receiving device 282 may wirelessly charge the battery of the electronics system 200 using any of a number of wireless charging techniques known in the art. The relay communication device 280 may be a hub 284 (e.g., a server). The hub 284 may be a communication hub with cellular connectivity. The hub 284 may be a device in the patient's home dedicated to communication with medical devices, such as the adaptor 10. The relay communication device 280 may be a mobile device 286, such as, for example, a mobile phone or tablet. In some embodiments, the mobile device 286 may be a laptop computer, a desktop computer, a wearable such as a connected watch, etc. More than one mobile device 286 may be in communication with the adaptor 10. Further, the adaptor 10 may in communication more than one of the devices 280. For example, the adaptor 10 may be in communication with both the receiving device 282 and the mobile device 286.

The relay communication device 280 may provide immediate and real time feedback to a user of the adaptor 10. For example, depth of breath may be instantly reported on the relay communication device 280 so that the user knows if deeper (or shallower) breaths should be taken. On the other hand, the duration of a current therapy may be communicated on the relay communication device 280 so that the user knows how long the current therapy session has lasted. As further example, automatic reminders may be communicated to the relay communication device 280 from the adaptor 10 to use the nebulizer. In some embodiments, the current battery charge of the adaptor 10 may be communicated to the relay communication device 280.

The network 300 may include one or more communication networks. The network 300 may include a clod 310. This may be a COPD cloud dedicated to communications related to medical data, such as nebulizer usage data for COPD patients. The network 300 may include one or more continuous communication nodes 320. The communication may be continuous such that continuous, e.g., real time, data is provided to these nodes 320. The nodes 320 may be in data continuous communication with the cloud 310. The nodes 320 may include one or more patient devices 322 and/or one or more home care devices 324. The patient device 322 and/or home care device 324 may be similar to the relay communication device 280, hub 284, or mobile device 288 as described above. The patient device 322 may belong to the patient, or related parties such as family members, such that communications are received by the patient, or the slated parties such as family members, via the device 322. The home care device 324 may belong to a home care provider, nursing facility, etc.

The network 300 may include one or more continuous communication nodes summary communication device 330. The communication may be intermittent such that summary data is provided to these nodes 320. The summary data may be summaries of one or more therapy sessions, for example data relating to a week or month of therapy. The nodes 330 may include one or more provider devices 332 and/or one or more payer devices 334. The provider device 332 may similar to the mobile device 286 described above. The provider device 332 may belong to a healthcare provider, e.g., a doctor, or other party interested in reviewing the data to provide medical assessments of the related therapy. The payer device 334 may belong to a payer of healthcare, e.g., an insurance company, or other party interested in reviewing the data to provide payment for the related therapy.

The various components of the system 6 may be used for a variety of assessments and improvements of inhalation therapy. Assessments may be made of the compliance of therapeutic sessions with inhalers, such as nebulizers, to improve the therapy. For instance, a patient may not be taking enough breaths with the nebulizer or may not be taking deep enough breaths. The determined indicator of compliance may communicate information to the patient or other parties that a higher quantity and/or deeper breaths should be taken. Further, adherence to prescribed inhalation therapy regimens may be improved. For instance, the system 6 may monitor the frequency of use of the inhaler or analyze the inhaled breaths over a period of time. If a patient is not using the inhaler enough, or is using it too much, the determined indicator of compliance may communicate information to the patient or other parties that the patient is not adhering to the regimen. In some embodiments, alerts regarding compliance or adherence may be sent to the patient via the relay communication device 280 or to the other parties via the network 300. These are just some examples of how the system 6 and the devices thereof may be used to improve the compliance with inhalation therapies. Other uses of the systems, devices and methods described herein will be apparent to those skilled in the art.

FIGS. 16-21 are flowcharts showing embodiments of methods for using the adaptor 10 to assess nebulizer therapy. The methods of FIGS. 16-21 may be performed with the various systems and devices described herein, such as with the system 2 and/or system 6 using the adaptor 10. The methods may be performed with these systems and devices to generate the various data plots described herein, such as the plots 500 and 550, to determine an indicator of the compliance with the nebulizer, as further described herein.

FIG. 15 shows an embodiment of a method 700 for using the adaptor 10 to assess nebulizer therapy. The method 700 may include block 710, wherein one or more physical property attributes are detected. Block 710 may be performed in the various manners described herein, for example with the sensors 210 and/or 212 to detect attributes, such as pressure, temperature, partial pressure or percentage of carbon dioxide, oxygen, nitrogen, water vapor and/or suspended liquid of fluid flowing within the channel 150 of the adaptor 10 or user touch or proximity of the user to the nebulizer accessory. In block 710, the electronics system 200 may be used to detect the attributes, as described herein.

The method 700 may also include block 712, wherein flow and/or proximity data is determined based on the detected attributes. In block 712, the determined flow and/or proximity data may be the data 505 or 555 described herein with respect to FIGS. 13 and 14. In some embodiments, the determined flow and/or proximity data in block 712 may be the results of calculations performed on such data, such as the calculated flow rate and/or direction of flow. Block 712 may be performed by the adaptor 10, such as with the electronics system 200.

The method 700 may also include block 714, wherein the flow data is communicated to one or more devices that are separate from the adaptor 10. In block 714, the communication circuit 250 may communicate the flow data to the one or more devices. Such devices in block 714 may be the receiving devices 280 described herein. In some embodiments, the devices in block 714 may be any of the device's in the network 300, as described herein. After the method 700 is performed, these and other receiving devices may receive such data and calculate an indicator of compliance with the nebulizer, which indicator may then be communicated to the user or other parties for assessment, evaluation, etc., of the nebulizer therapy.

Figure 17:
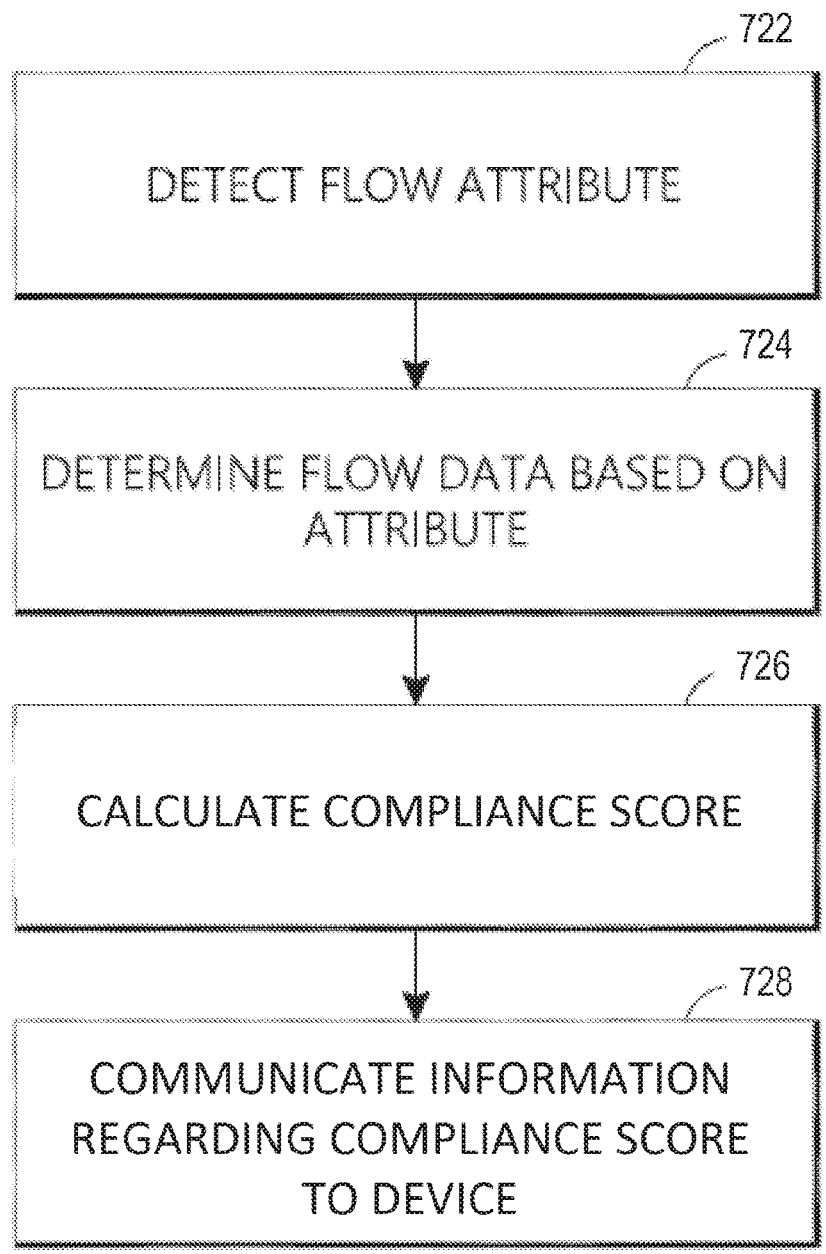
FIG. 17 is a flowchart showing another embodiment of a method for using the various nebulizer adaptors described herein to assess nebulizer therapy.

FIG. 17 shows an embodiment of a method 720 for using the adaptor 10 to assess nebulizer therapy. The method 700 may include block 722, wherein one or more flow attributes are detected. Block 722 may be the came or similar as block 710 of the method 700 shown in FIG. 18. The method 720 may also include block 724, wherein flow data is determined based on the detected attributes. Block 724 may be the same or similar as block 712 of the method 700 shown in FIG. 16.

The method 720 may also include block 726, wherein an indicator of compliance with therapy is calculated. In some embodiments, the indicator may be calculated as described herein with respect to FIGS. 4-14. The electronics system 200 may perform the calculation. The method 720 may also include block 728, wherein the indicator of compliance is communicated to one or more devices that are separate from the adaptor 10. In block 728, the communication circuit 250 may communicate the indicator to the one or more devices. Such devices in block 728 may be the receiving devices 280 described herein. In some embodiments, the devices in block 728 may be the devices in the network 300, as described herein. After the method 720 is performed, these and other receiving devices may communicate the indicator to the user or other parties for assessment, evaluation, etc., of the nebulizer therapy.

Figure 18:
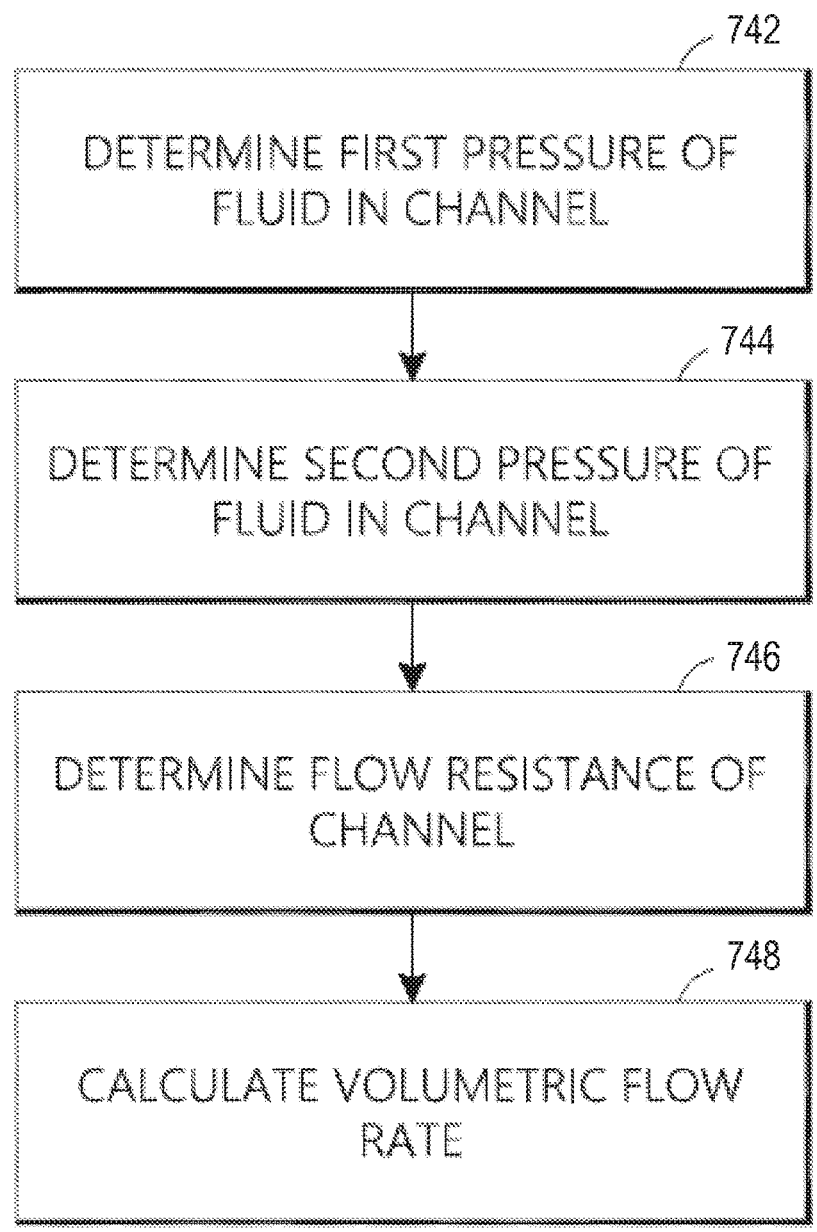
FIG. 18 is a flowchart showing another embodiment of a method for using the various nebulizer adaptors described herein to assess nebulizer therapy.
Figure 19:
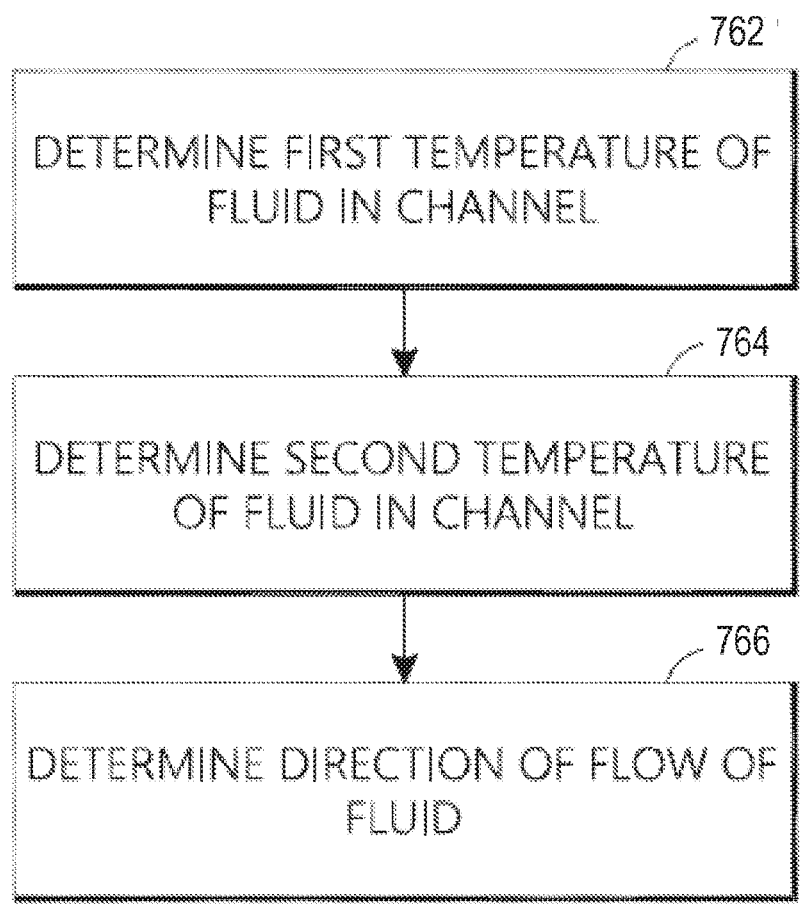
FIG. 19 is a flowchart showing another embodiment of a method for using the various nebulizer adaptors described herein to assess nebulizer therapy.

FIG. 18 shows an embodiment of a method 740 for determining the volumetric flow rate of fluid flowing through the adaptor 10. The volumetric flow rate may be used to determine an indicator of the compliance with a nebulizer, as described herein.

The method 740 may begin with block 742, wherein a first pressure of the fluid is determined. The pressure may be determined in block 742 as described herein, for example, with respect to FIG. 4. Thus, for example, the pressure may be determined in block 742 at a first location of the channel 150 of the adaptor 10, which may be in the first channel region 152. Block 742 may be performed with the electronics system 200, such as with the sensor 210 or 212.

The method 740 may also include block 744, wherein a second pressure of the fluid is determined. The second pressure may be determined in block 742 as described herein, for example, with respect to FIG. 4. Thus, for example, the second pressure may be determined in block 742 at a second location of the channel 150 of the adaptor 10, which may be in the third channel region 158. Block 744 may be performed with the electronics system 200, such as with the sensor 210 or 212.

The method 740 may also include block 746, wherein the flow resistance of the channel 150 is determined. The flow resistance may be determined in block 748 as described herein, for example with respect to FIG. 4. Thus, the flow resistance may be the resistance to flowing fluid of the second channel region 154. This resistance may be pre-determined, for example, based on pre-determined geometry of the channel 150 for a given adaptor 10. Thus, determination of the resistance in block 746 may include accessing such data for the given adaptor 10 using the electronics system 200 (e.g., from the memory 240 or as communicated via the communication circuit 250 from a separate communication device).

The method 740 may also include block 748, wherein the volumetric flow rate is determined. The volumetric flow rate may be determined as described herein, for example as described with respect to FIG. 4. The volumetric flow rate in block 748 may be determined using the electronics system 200, such as with instructions from the program module 230 that configure the processor 220 to perform the relevant calculations. In some embodiments, block 748 may be performed by a separate device. For instance, the pressures and resistance determined in blocks 742, 744 and 746 may be communicated to a separate device, such as the receiving relay communication device 280 or devices of the network 300, and these separate devices may then calculate the volumetric flow rate.

FIG. 15 shows an embodiment of a method 760 for determining the direction of flow of fluid flowing through the adaptor 10. The direction of flow may be used to determine an indicator of the compliance with a nebulizer, as described herein.

The method 760 may begin with block 762 wherein a first temperature of the fluid flowing through the channel 150 is determined. The temperature may be determined in block 762 as described herein, for example with respect to FIG. 5. Thus, for example, the temperature of the fluid of the channel 150 of the adaptor 10 may be determined in block 762 at a first point in time. Block 762 may be performed with the electronics system 200, such as with the sensor 210 or 212.

The method 760 may also include block 764, wherein a second temperature of the fluid is determined. The second pressure may be determined in block 764 as described herein, for example, with respect to FIG. 6. Thus, for example, the temperature of the fluid of the channel 150 of the adaptor 10 may be determined in block 764 at a second point in time. The temperatures detected in blocks 762 and 764 may be in the same location of the channel 150. In some embodiments, the temperatures detected in blocks 762 and 764 may be in different locations of the channel 150. Block 764 may be performed with the electronics system 200, such as with the sensor 210 or 212.

The method 760 may also include block 766, wherein the direction of flow of the fluid within the channel 150 is determined. The direction of flow may be determined in block 766 as described herein, for example, with respect to FIG. 6. The direction of flow hi block 766 may be determined using the electronics system 200, such as with instructions from the program module 230 that configure the processor 220 to perform the relevant calculations. In some embodiments, block 766 may be performed by a separate device. For instance, the temperatures determined in blocks 762 and 764 may be communicated to a separate device, such as the receiving relay communication device 280 or devices of the network 300, and these separate devices may then calculate the direction of flow.

Figure 20:
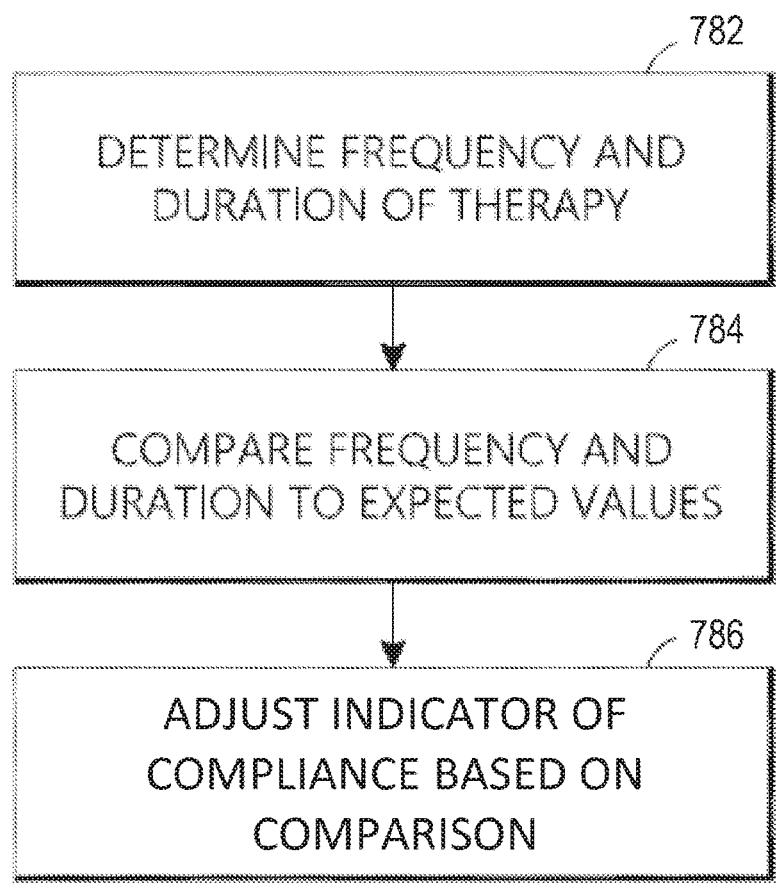
FIG. 20 is a flowchart showing another embodiment of a method for using the various nebulizer adaptors described herein to assess nebulizer therapy.

FIG. 20 shows an embodiment of a method 780 for determining an indicator of compliance with a nebulizer using the adaptor 10 based on frequency and/or duration of therapy. The method 780 may be performed by the adaptor 10, such as with the electronics system 200. The method 780 may be performed by a device separate from the adaptor 10, such as with the receiving relay communication device 280 or with any of the devices of the network 300. In some embodiments, some blocks of the method 780 may be performed by the adaptor 10 and other blocks may be performed by a separate device.

The method 780 may begin with block 782, wherein the frequency and/or duration of therapy with the nebulizer is determined. In block 782, the frequency and/or duration of therapy may be determined as described herein, for example with respect to FIGS. 4-14. Block 782 may be performed by the adaptor 10, such as with the electronics system 200. Block 782 may be performed by separate devices after receiving the relevant flow data from the adaptor 10. For instance, the data 505 or 555 may be received by the relay communication device 260, which may then analyze such data to determine the frequency and/or duration.

The method 780 may also include block 784, wherein the frequency and/or duration are compared to expected values. Block 784 may be performed as described herein, for example with respect to FIGS. 13 and 14. Block 784 may be performed by the adaptor 10, such as with the electronics system 200. Block 784 may be performed by separate devices alter receiving the relevant flow data from the adaptor 10. For instance, data related to the determined frequency and/or duration of therapy may be received by the relay communication device 280, which may then compare such data to expected values.

The method 780 may also include block 786, wherein the indicator of compliance with therapy is adjusted or otherwise determined. The indicator in block 786 may be determined, adjusted, etc., as described herein, for example with respect to FIGS. 13 and 14. Block 786 may be performed by the adaptor 10, such as with the electronics system 200. Block 786 may be performed by separate devices after receiving from the adaptor 10 comparisons of the frequency and/or duration data to expected values. For instance, such comparisons may be received by the relay communication device 280, which may then determine the indicator of compliance.

Figure 21:
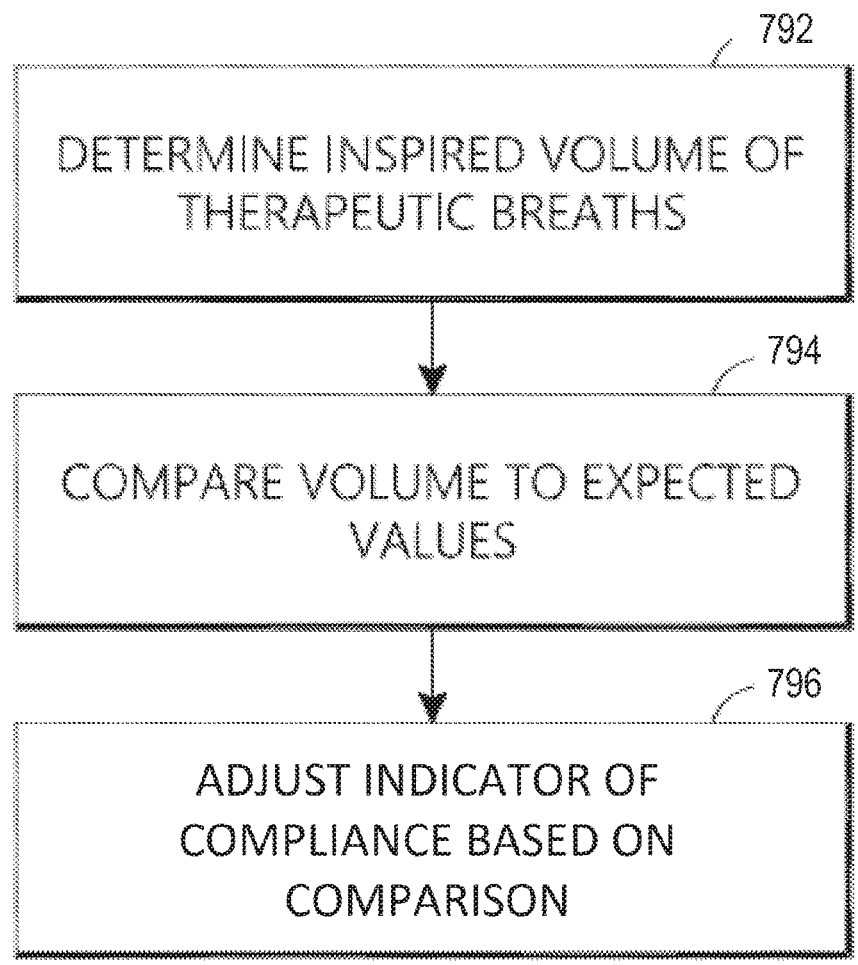
FIG. 21 is a flowchart showing another embodiment of a method for using the various nebulizer adaptors described herein to assess nebulizer therapy.

FIG. 21 shows an embodiment of a method 790 for determining an indicator of compliance with a nebulizer using the adaptor 10 based on volumetric flow rate. The method 790 may be performed by the adaptor 10, such as with the electronics system 200. The method 790 may be performed by a device separate from the adaptor 10, such as with the receiving relay communication device 280 or with any of the devices of the network 300. In some embodiments, some blocks of the method 790 may be performed by the adaptor 10 and other blocks may be performed by a separate device.

The method 790 may begin with block 792, wherein the inspired volume of therapeutic breaths during therapy with the nebulizer is determined. In block 792, the inspired volume of therapeutic breaths may be determined as described herein, for example, with respect to FIGS. 4-14. Block 792 may be performed by the adaptor 10, such as with the electronics system 200. Block 792 may be performed by separate devices after receiving the relevant flow data from the adaptor 10. For instance, the data 505 or 555 may be received by the relay communication device 280, which may then analyze such data to determine the inspired volume of therapeutic breaths.

The method 790 may also include block 794, wherein the inspired volume of therapeutic breaths are compared to expected values. Block 794 may be performed as described herein, for example with respect to FIG. 14. Block 794 may be performed by the adaptor 10, such as with the electronics system 200. Block 794 may be performed by separate devices after receiving the relevant flow data from the adaptor 10. For instance, data related to the inspired volume of therapeutic breaths may be received by the relay communication device 280, which may then compare such data to expected values.

The method 790 may also include block 796, wherein the indicator of compliance is adjusted or otherwise determined. The indicator in block 796 may be determined, adjusted, etc. as described herein, for example, with respect to FIG. 14. Block 796 may be performed by the adaptor 10, such as with the electronics system 200. Block 796 may be performed by separate devices after receiving from the adaptor 10 comparisons of the inspired volume data to expected values. For instance, such comparisons may be received by the relay communication device 280, which may then determine the indicator of compliance.

In various embodiments, the adaptor may work with a variety of nebulizers. Some nebulizer types include vibrating mesh, piezo/ultrasonic, static mesh, and jet/compression. The nebulizers may be used for a variety of conditions, including cystic fibrosis, asthma, COPD and other respiratory diseases. The adaptor has fittings to attach to standard-sized nebulizers thus providing a "universal" adaptor for patients. The adaptor may have a first fitting configured to couple with a portion of the nebulizer. The adaptor may also have a second fitting for attaching to a facemask or other nebulizer accessory. For example, the accessory may be configured to receive a standard facemask or other nebulizer accessory on the opposite side of the adaptor as the nebulizer.

The adaptor may include a variety of electronics. The adaptor may include one or more sensors, a processor and a communication circuit. This may include, for example, a pressure sensor, a temperature sensor, humidity sensor, carbon dioxide sensor, capacitive touch sensor, a processor, a memory, a communication circuit, a battery, a second communication device, and/or other electronics as described below. Thus, the technology relates to an adaptor with "smart" capabilities that can be used with inhalers, including but not limited to nebulizers, for evaluation and communication of information related to the evaluation. The adaptor may be integrated with a network system, such as a mobile device and/or cellular or cloud network, for assessing and improving patient usage, e.g., adherence, of the nebulizer.

The adaptor may have communication connectivity, such as Bluetooth or short range similar wireless communication protocol(s). It may also have a variety of other near field communication (NFC) or other communication features. Some versions of the adaptor may have cellular, radio or other connectivity capability. The adaptor may thus communicate with a variety of communication devices, including, but not limited to, cell phones, tablets, and watches, or various other communication devices that may or may not be mobile.

The adaptor may also communicate with network systems such as the internet or the cloud. The adaptor may communicate with such networks directly. The adaptor may communicate with such systems indirectly via intermediate devices. Such intermediate devices may include, for example, mobile devices, or Bluetooth/cellular hubs like the Qualcomm 2NET® hub, etc. These and other systems may then communicate with the patient, with a healthcare provider, with a healthcare payer, and/or other parties.

The adaptor may be used with these and other communication systems for a variety of purposes. Some purposes may include patient adherence monitoring, tracking, reporting, etc. and patient coaching. The adaptor may generate via the adaptor's electronics (e.g., a microprocessor) patient adherence scores and identify non-adherent patients for providers/payers (e.g., statistical distribution of patient adherence). The adaptor may record and report on embodiments of therapy sessions, such as duration and start/slop times. The adaptor, via a display on the adaptor or on a mobile device, may provide visual stimulus (e.g., light gamification) to motivate deeper inspirations throughout the entire length of therapy. The adaptor may assess the volume of each therapeutic breath, as detected by the sensor(s) (e.g., mass airflow sensor and/or pressure sensor) of the adaptor, to report therapy compliance. The adaptor may automate medication reminders.

The adaptor may include one or more of a variety of sensors. There may be a temperature sensor, humidity sensor, mass airflow sensor, carbon dioxide sensor, capacitive touch sensor, and/or pressure sensor to analyze and/or track breaths. For example, the temperature differential between inhale and exhale may be used to determine a change in direction of airflow. As another example, one or more pressure sensors such as a diaphragm may be implemented. Deflections of the diaphragm may correlate to breaths. For instance, these or other sensors may generate a voltage in proportion to the amount and/or direction of the flow of air, or a voltage that exceeds a threshold in response to a breath. Analysis of such data may be performed to generate parameters and/or determine indications of the compliance with the nebulizer. Relevant parameters may include volumetric how rate, volume of inhaled fluid, direction of flow, quantity of breaths, frequency of breaths, duration of therapy, and others.

In some embodiments, en apparatus for a nebulizer is used. The apparatus includes a body extending from a proximal portion to a distal portion and having an inner portion and an outer portion, the proximal portion including a first fitting configured to couple with a nebulizer accessory, the distal portion having a second fitting configured to couple with the nebulizer, the inner portion of the body defining a channel that fluidity connects the proximal and distal portions, a flow sensor coupled with the body, the flow sensor in fluid communication with the channel and configured to detect at least one attribute of a fluid flowing within the channel, a communication transmitter, and a processor operatively coupled with the flow sensor and the transmitter, the processor configured to: determine flow data based at least in part on the detected attribute of the fluid; and instruct the transmitter to send information regarding the flow data to a receiving device.

In some embodiments, the flow sensor includes a pressure sensor and the detected attribute includes a pressure. In some embodiments, the processor is further configured to determine a volumetric flow rate of the flowing fluid based at least in part on the detected pressure. In some embodiments, determining of the volumetric flow rate of the flowing fluid is based al least in part on i) determining a first pressure of the flowing fluid at a first location of the channel, ii) determining a second pressure of the flowing fluid at a second location of the channel, and iii) determining a flow resistance of a portion of the channel located generally in between the first and second locations, wherein the flow resistance is based at least in part on a geometry of at least the portion of the channel located generally in between the first and second locations. In some embodiments, the processor is further configured to calculate an indicator of a compliance with therapy associated with the flowing fluid based at least in part on the volumetric flow rate. In some embodiments, the processor is further configured to code the information regarding the flow data for transmission to and analysis by the receiving device to generate an indicator of a compliance with therapy associated with the flowing fluid based at least in part on the volumetric flow rate. In some embodiments, the flow sensor includes a temperature sensor and the detected attribute includes temperature. In some embodiments, the processor is further configured to determine a direction of flow of the fluid through the channel based at least in part on the detected temperature. In some embodiments, determining of the direction of flow of the fluid through the channel is based at least in part on i) determining a first temperature of the fluid at a first point in time and ii) determining a second temperature of the flowing fluid at a second point in time in some embodiments, the processor is further configured to generate an indicator of a compliance with therapy associated with the flowing fluid based at least in part on the determined direction of flow of the fluid through the channel. In some embodiments, the processor is further configured to code the information regarding the flow data for transmission to and analysis by the receiving device to generate an indicator of a compliance with therapy associated with the flowing fluid based at least in part on the coded information. In some embodiments, the flow sensor further includes a temperature sensor and the detected attribute further includes a temperature, wherein the processor is further configured to determine a direction of flow of the fluid through the channel based at least in part on the detected temperature, wherein the determining the direction of flow of the fluid through the channel is based at least in part on i) determining a first temperature of the fluid at a first point in time and ii) determining a second temperature of the flowing fluid at a second point in time. In some embodiments, the processor is further configured to generate an indicator of a compliance with therapy associated with the flowing fluid based at least in part on the volumetric flow rate and/or on the determined direction of flow of the fluid through the channel. In some embodiments, the processor is further configured to code the information regarding the flow data for transmission to and analysis by the receiving device to generate an indicator of compliance with therapy associated with the flowing fluid. In some embodiments, the receiver is a mobile device or a communications hub. In some embodiments, the first fitting is located across from the second fitting. In some embodiments, the first fitting is located angularly 160 degrees relative to the second fitting. In some embodiments, the first fitting can fit at least partially around the nebulizer. In some embodiments, the first fitting can fit at least partially inside the nebulizer. In some embodiments, a continuous flow path is created from the nebulizer to the nebulizer accessory when the apparatus is coupled to both the nebulizer and the nebulizer accessory.

In another embodiment, a method, operable by an adaptor for a nebulizer, the adaptor having a body with an inner portion defining a channel therethrough, a flow sensor, a communication transmitter, and a processor, is disclosed.

The method includes detecting, via the flow sensor, at least one attribute of a fluid flowing within the channel of the body; determining, at the processor, flow data based at least in part on the detected attribute of the fluid; and sending, via the communication transmitter, information regarding the flow data to a receiving device that is separate from the apparatus.

In some embodiments, the method further includes coding the flow data, wherein sending the information includes transmitting, via the communication transmitter, the coded flow data to the receiving device, the receiving device configured to generate an indicator of a compliance with therapy associated with the flowing fluid based at least in part on the coded flow data. In some embodiments, the method further includes calculating an indicator of a compliance with therapy associated with the flowing fluid based at least in part on the flow data; and coding the indicator; wherein sending the information includes transmitting, via the communication transmitter, the coded indicator to the receiving device. In some embodiments, the flow sensor includes a pressure sensor, wherein the detected attribute includes a pressure, and wherein the method further includes determining a volumetric flow rate of the flowing fluid based at least in part on the detected pressure. In some embodiments, determining the volumetric flow rate of the flowing fluid includes: determining a first pressure of the flowing fluid at a first location of the channel: determining a second pressure of the flowing fluid at a second location of the channel; and determining a flow resistance of a portion of the channel located generally. In between the first and second locations. In some embodiments, the flow sensor includes a temperature sensor, wherein the detected attribute includes a temperature, and wherein the method further includes determining a direction of flow of the fluid through the channel based at least in part on the detected temperature. In some embodiments, determining a direction of flow of the fluid through the channel includes: determining a first temperature of the fluid at a first point in time; and determining a second temperature of the flowing fluid at a second point in time.

In another embodiment, a non-transitory computer readable storage medium is disclosed. The non-transitory computer readable storage medium has stored thereon instructions that, when executed by a processor of a nebulizer adaptor, cause the processor to: detect, via a flow sensor of the adaptor, at least one attribute of a fluid flowing within the adaptor; determine flow date based at least in part on the detected attribute of the fluid; and send, via a communication transmitter of the adaptor, information regarding the flow data to a receiving device that is separate from the adaptor.

In some embodiments of the non-transitory computer readable medium, the instructions further cause the processor to code the flow data, wherein sending the information includes transmitting, via the communication transmitter, the coded flow data to the receiving device, the receiving device configured to generate an indicator of a compliance with therapy associated with the flowing fluid based at least in part on the coded flow data. In some embodiments, the instructions further cause the processor to: calculate an indicator of a compliance with therapy associated with the flowing fluid based at least in part on the flow data; and code the indicator, wherein the information regarding the flow data includes the coded indicator. In some embodiments, the flow sensor includes a pressure sensor, wherein the detected attribute includes a pressure, and wherein the instructions further cause the processor to determine a volumetric flow rate of the flowing fluid based at least in part on the detected pressure. In some embodiments, determining the volumetric flow rate of the flowing fluid includes: determining a first pressure of the flowing fluid at a first location of the channel; determining a second pressure of the flowing fluid at a second location of the channel; and determining a flow resistance of a portion of the channel located generally in between the first and second locations. In some embodiments, the flow sensor includes a temperature sensor, wherein the detected attribute includes a temperature, and wherein the instructions further cause the processor to determine a direction of flow of the fluid through the channel based at least in part on the detected temperature. In some embodiments, determining a direction of now of the fluid through the channel includes determining a first temperature of the fluid at a first point in time; and determining a second temperature of the flowing fluid at a second point in time.

In another embodiment, another non-transitory computer readable storage medium is disclosed. The non-transitory computer readable storage medium has stored thereon instructions that, when executed by a processor of a device paired with a nebulizer adaptor, cause the processor to: receive, via a communication receiver of the device, information from the adaptor including encoded flow data regarding a fluid delivered to a patient via the adaptor and the nebulizer, decode the encoded flow data; and calculate an indicator of a compliance with therapy delivered to the patient based on the decoded flow data.

In some embodiments of the non-transitory computer readable medium, calculating the indicator includes determining a volumetric flow rate of the fluid flowing within the channel of the adaptor apparatus based at least in part on i) a detected pressure of the fluid flowing within the channel and ii) a determined flow resistance of a portion of the channel. In some embodiments, calculating the indicator includes determining a direction of flow of the fluid through the channel based at least in part on a detected temperature of the fluid flowing within the channel. In some embodiments, the instructions further cause the processor to communicate the indicator to the user of the receiving device.

In another embodiment, a method, operable by a device paired with a nebulizer adaptor, the device having a communication transceiver and a processor, is disclosed. The method includes receiving, at the transceiver, via wireless communication with the adaptor, information including encoded flow data regarding a fluid delivered to a patient via the adaptor and the nebulizer; decoding the encoded flow data; and calculating an indicator of a compliance with therapy delivered to the patient based on the decoded flow data.

In another embodiment, a method for generating a compliance score indicative of a compliance with therapy with a nebulizer is disclosed, the nebulizer having an adaptor apparatus that includes a body defining a channel therethrough, a flow sensor, a communication transmitter and a processor. The method includes detecting, at the flow sensor, at least one attribute of a fluid flowing within the channel of the body; determining, at the processor, flow data based at least in part on the detected attribute of the fluid, wherein the determined flow data can be analyzed to determine the compliance score; and sending, via the communication transmitter, information regarding at least one of the flow data or the compliance score to a receiving device, wherein the receiving device is separate from the apparatus and can communicate the compliance score to a user.

In another embodiment, a non-transitory computer readable medium is disclosed that includes instructions stored thereon that, when executed by at least one processor of an adaptor apparatus for a nebulizer, cause the processor to perform a process for generating a compliance score indicative of a compliance with therapy with the nebulizer, the adaptor apparatus including a body defining a channel therethrough, a flow sensor, a communication transmitter and a processor. The process includes detecting al least one attribute of a fluid flowing within the channel of the body; determining flow data based at least in part on the detected attribute of the fluid, wherein the determined flow data can be analyzed to determine the compliance score; and sending information regarding the flaw data or the compliance score to a receiving device, wherein the receiving device is separate from the adaptor apparatus and can communicate the compliance score to a user.

In another embodiment, a non-transitory computer readable medium is disclosed including instructions stored thereon that when executed by at least one processor of a device perform a process for communicating to a user of the device a compliance score indicative of a compliance with therapy performed with a nebulizer. The process includes receiving, via wireless communication from an adaptor apparatus of the nebulizer, information from the adaptor apparatus of the nebulizer, wherein the nebulizer is separate from the receiving device, wherein the adaptor apparatus can detect at least one attribute of a fluid flowing within a channel of the adaptor apparatus, to determine flow data based at least in part on the detected attribute of the fluid, and to send the information to the receiving device, wherein the information is regarding at least one of the flow data or the compliance score, and wherein the determined flow data can be analyzed to determine the compliance score: and communicating the compliance score to the user of the receiving device.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others. The scope of the invention is indicated by the appended claims rather than by the foregoing description. All changes which come within the meaning and range of equivalency of the claims are to be embraced within their scope.

In addition, the drawings depict only several embodiments in accordance with the disclosure for illustrative purposes, but are not meant to be limiting. Other embodiments may be utilized, and other changes may be made, without departing from the spirit or scope of the subject matter presented here. It will be readily understood that the aspects of the present disclosure, as generally described herein and illustrated in the figures, can be arranged, substituted, combined, and designed in a wide variety of different configurations, all of which are explicitly contemplated and make part of this disclosure.

The logical blocks, modules and flow chart sequences are illustrative only. A person of skill in the art will understand that the steps, decisions, and processes embodied in the flowcharts described herein may be performed in an order other than that described herein. Thus, the particular flowcharts and descriptions are not intended to limit the associated processes to being performed in the specific order described.

The various illustrative logical blocks, modules, and method steps described in connection with the embodiments disclosed herein may be implemented as electronic hardware, software stored on a computer readable medium and executable by a processor, or combinations of both. To dearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. Artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A software module may reside in RAM memory, flash memory, ROM memory, EPROM memory, EEPROM memory, registers, hard disk, a removable disk, a CD-ROM, or any other form of storage medium known in the art. An exemplary memory, which may include a storage medium, is coupled to the processor such that the processor reads information from, and writes information to, the memory storage medium. In the alternative, the storage medium may be integral to the processor. The processor and the storage medium may reside in an ASIC.

A person skilled in the art will recognize that each of these sub-systems may be inter-connected and controllably connected using a variety of techniques and hardware and that the present disclosure is not limited to any specific method of connection or connection hardware.

The technology is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, a microcontroller or microcontroller based system, programmable consumer electronics, network PCs, minicomputers, mainframe computers, distributed computing environments that include any of the above systems or devices, and the like.

As used herein, instructions refer to computer-implemented steps for processing information in the system. Instructions may be implemented in software, firmware or hardware and include any type of programmed step undertaken by components of the system.

A microprocessor may be any conventional general purpose single- or multi-chip microprocessor such as a Pentium® processor, a Pentium® Pro processor, a 8051 processor, a MIPS® processor, a Power PC® processor, an Alpha® processor, or a duo core or quad core processor. In addition, the microprocessor may be any conventional special purpose microprocessor such as a digital signet processor or a graphics processor. The microprocessor typically has conventional address lines, conventional data lines, and one or more conventional control lines.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In this description, like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede anti; or lake precedence over any such contradictory material The term "comprising" as used herein is synonymous with "including," "containing," or "characterized by," and is inclusive or open-ended and does not exclude additional, unrecited elements or method steps.

All numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The foregoing description details certain embodiments of the systems, devices, and methods disclosed herein. It will be appreciated, however, that no matter how detailed the foregoing appears in text, the systems, devices, and methods may be practiced in many ways. As is also stated above, it should be noted that the use of particular terminology when describing certain features or aspects of the invention should not be taken to imply that the terminology is being redefined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment may be included with other depicted embodiments in any combination. For example, any of the various components described herein and/or depicted in the figures may be combined, interchanged or excluded from other embodiments.

The above description discloses several methods, devices and systems of the present invention. This invention is susceptible to modifications in the methods, devices and systems. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the following claims. Therefore, although this invention has been disclosed in the context of certain preferred embodiments and examples, it will be understood by those skilled in the art that the present invention extends beyond the specifically disclosed embodiments to other alternative embodiments and/or uses of the invention and equivalents thereof. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

The invention claimed is:

1. A method for assisting a user to comply with a nebulizer therapy treatment, the method comprising:
determining, by a nebulizer therapy accessory, a start timestamp indicating a time at which a signal from a sensor configured to indicate a physical parameter generated by a body of the user has reached a threshold value, wherein the nebulizer therapy accessory is at least one of a mouthpiece, an adaptor, or a mask;
recording the start timestamp as a start of a treatment duration;
starting, by the nebulizer therapy accessory, a treatment timer at the start timestamp;
determining a stop timestamp, wherein the determining the stop timestamp comprises:
determining that the signal has not exceeded the threshold value for a first time period;
determining that the first time period exceeded a timeout value; and
recording the stop timestamp as an end of the treatment duration, wherein the stop timestamp indicates a time at which the signal reached the threshold value prior to an end of the first time period;
determining a pause in treatment, wherein the determining the pause in treatment comprises:
determining that a time period between successive threshold crossings of the signal is greater than a pause timeout value and less than the timeout value, wherein the pause timeout value is less than the time out value; and
recording the time period as a pause duration;
calculating an actual treatment duration by subtracting the start timestamp from the stop timestamp to provide the treatment duration and subtracting the pause duration from the treatment duration to provide the actual treatment duration; and
transmitting, by the nebulizer therapy accessory, the actual treatment duration to a relay communication device to determine a compliance score.

2. The method of claim 1, wherein the timeout value is greater than 1 minute.

3. The method of claim 1, further comprising:
determining, by the relay communication device communicatively coupled to the nebulizer therapy accessory, the compliance score for the nebulizer therapy treatment, wherein determining the compliance score comprises comparing the actual treatment duration to an expected treatment duration, wherein the expected treatment duration is predetermined based on a treatment characteristic regarding a nebulizer; and
transmitting, by the relay communication device, an alert including the compliance score to a user device via a communication network.

4. The method of claim 1, wherein the pause timeout value is greater than 15 seconds.

5. The method of claim 1, wherein the pause timeout value is greater than 30 seconds.

6. The method of claim 1, wherein the nebulizer therapy accessory is the mouthpiece.

7. The method of claim 1, wherein the nebulizer therapy accessory is the adaptor.

8. The method of claim 1, wherein the nebulizer therapy accessory is the mask.

9. The method of claim 1, wherein the physical parameter is selected from the group consisting of a temperature of a fluid, a humidity of a fluid, a pressure, a volumetric flow rate, a volume of a fluid, a proximity of the user's body to the nebulizer therapy accessory, a carbon dioxide concentration of a fluid, and a pressure of a fluid.

10. The method of claim 1, wherein the sensor is a temperature sensor, and wherein the physical parameter is a change in temperature of a fluid flowing through the nebulizer therapy accessory.

11. The method of claim 1, wherein the sensor is a humidity sensor, and wherein the physical parameter is a change in humidity of a fluid flowing through the nebulizer therapy accessory.

12. The method of claim 1, wherein the sensor is a mass airflow sensor, and wherein the physical parameter is a change in volume of a fluid flowing through the nebulizer therapy accessory.

13. The method of claim 1, wherein the sensor is a capacitive touch sensor, and wherein the physical parameter is a change in proximity of the user's body to the nebulizer therapy accessory.

14. The method of claim 1, wherein the sensor is a carbon dioxide sensor, and wherein the physical parameter is a change in carbon dioxide concentration of a fluid flowing through the nebulizer therapy accessory.

15. The method of claim 1, wherein the sensor is a pressure sensor, and wherein the physical parameter is a change in pressure of a fluid flowing through the nebulizer therapy accessory.

16. The method of claim 1, wherein the sensor is a first sensor, the physical parameter is a first physical parameter, and the threshold value is a first threshold value, and wherein the start timestamp further indicates a time at which a signal from a second sensor configured to indicate a second physical parameter generated by the user's body has reached a second threshold value.

17. The method of claim 1, wherein the transmitting, by the nebulizer therapy accessory, the actual treatment duration to the relay communication device to determine the compliance score comprises:
transmitting, by the nebulizer therapy accessory and via a near field communication protocol (NFC), the actual treatment duration to the relay communication device to determine the compliance score.

18. A system for nebulizer therapy treatment, the system comprising:
a sensor configured to detect a physical parameter generated by a user's body and generate a signal indicative of the physical parameter;
a nebulizer therapy accessory comprising at least one of a mouthpiece, an adaptor or a mask, the nebulizer therapy accessory configured to:
determine a start timestamp indicating a time at which the signal from the sensor has reached a threshold value;
record the start timestamp as a start of a treatment duration;

start a treatment timer at the start timestamp:

determine a stop timestamp based on a first time period exceeding a timeout value, over which the signal has not exceeded the threshold value;

record the stop timestamp as an end of the treatment duration;

determine a pause in treatment, wherein when determining the pause in treatment, the nebulizer therapy accessory is configured to:

determine that a time period between successive threshold crossings of the signal is greater than a pause timeout value and less than the timeout value, wherein the pause timeout value is less than the time out value; and record the time period as a pause duration;

calculate an actual treatment duration by subtracting the start timestamp from the stop timestamp to provide the treatment duration and subtracting the pause duration from the treatment duration to provide the actual treatment duration; and transmit the actual treatment duration to a relay communication device, based on calculating the treatment duration, to determine a compliance score.

19. The system of claim 18, wherein the physical parameter is selected from the group consisting of a temperature of a fluid, a humidity of a fluid, a pressure, a volumetric flow rate, a volume of a fluid, a proximity of the user's body to the nebulizer therapy accessory, a carbon dioxide concentration of a fluid, and a pressure of a fluid.

20. A non-transitory computer-readable medium comprising program code, which when executed by a processor of a nebulizer therapy accessory comprising at least one of a mouthpiece, an adaptor or a mask, is configured to cause the processor to:

determine a start timestamp indicating a time at which a signal from a sensor configured to indicate a physical parameter generated by a user's body has reached a threshold value;

record the start timestamp as a start of a treatment duration;

start a treatment timer at the start timestamp;

determine a stop timestamp based on a first time period exceeding a timeout value, over which the signal has not exceeded the threshold value;

record the stop timestamp as an end of the treatment duration;

determine a pause in treatment, wherein the program code that causes the processor to determine the pause in treatment, causes the processor to:

determine that a time period between successive threshold crossings of the signal is greater than a pause timeout value and less than the timeout value, wherein the pause timeout value is less than the time out value; and record the time period as a pause duration;

calculate an actual treatment duration by subtracting the start timestamp from the stop timestamp to provide the treatment duration and subtracting the pause duration from the treatment duration to provide the actual treatment duration; and transmit the treatment duration to a relay communication device, based on calculating the actual treatment duration, to determine a compliance score.

21. The non-transitory computer-readable medium of claim 20, wherein the physical parameter is selected from the group consisting of a temperature of a fluid, a humidity of a fluid, a volumetric flow rate, a volume of a fluid, a proximity of the user's body to the nebulizer therapy accessory, a carbon dioxide concentration of a fluid, and a pressure of a fluid.

* * * * *